US012661332B1

(12) United States Patent
Yamaguchi et al.

(10) Patent No.: US 12,661,332 B1
(45) Date of Patent: Jun. 23, 2026

(54) EMOLLIENT COMPOSITIONS COMPRISING LINOLEIC ACID AND CONJUGATED LINOLEIC ACID AND METHODS OF USE

(71) Applicant: Primus Pharmaceuticals, Inc., Scottsdale, AZ (US)

(72) Inventors: Masayoshi Yamaguchi, Shizuoka (JP); James D. Weir, Scottsdale, AZ (US); Ryan E. Hartung, Scottsdale, AZ (US)

(73) Assignee: Primus Pharmaceuticals, Inc., Scottsdale, AZ (US)

( * ) Notice: Subject to any disclaimer, the term of this patent is extended or adjusted under 35 U.S.C. 154(b) by 0 days.

(21) Appl. No.: 19/074,477

(22) Filed: Mar. 10, 2025

Related U.S. Application Data

(63) Continuation of application No. PCT/US2024/058216, filed on Dec. 3, 2024.

(60) Provisional application No. 63/713,900, filed on Oct. 30, 2024, provisional application No. 63/567,428, filed on Mar. 20, 2024, provisional application No. 63/609,569, filed on Dec. 13, 2023, provisional application No. 63/605,621, filed on Dec. 4, 2023.

(51) Int. Cl.
| | |
|---|---|
| *A61K 31/201* | (2006.01) |
| *A61K 9/00* | (2006.01) |
| *A61K 47/18* | (2017.01) |
| *A61K 47/28* | (2006.01) |
| *A61P 17/00* | (2006.01) |

(52) U.S. Cl.
CPC .......... *A61K 31/201* (2013.01); *A61K 9/0014* (2013.01); *A61K 47/18* (2013.01); *A61K 47/28* (2013.01); *A61P 17/00* (2018.01)

(58) Field of Classification Search
CPC ...... A61K 31/201; A61K 8/361; A61K 47/18; A61K 47/28; A61K 8/63; A61K 8/68; A61P 17/06; A61Q 19/00
See application file for complete search history.

(56) References Cited

U.S. PATENT DOCUMENTS

| | | | |
|---|---|---|---|
| 2005/0186231 A1* | 8/2005 | Zhang .................... | A61K 8/361 |
| | | | 424/401 |
| 2017/0020798 A1* | 1/2017 | Elias ........................ | A61K 8/44 |

OTHER PUBLICATIONS

Badawy et al. Food Research International 2023 172 113158, p. 1-26.*
Du et al. Poultry science 2000, 79, 1749-1756.*
Bhogadi et al. Rasayan J. Chem. 2014, 7(4), 380-389.*
EpiCeram Prescribing Information, Jan. 1, 2020, 1 pg.
EpiCeram 510(k) Summary, Apr. 11, 2006, 5 pp.

* cited by examiner

*Primary Examiner* — Irina Neagu
(74) *Attorney, Agent, or Firm* — Clark G. Sullivan

(57) ABSTRACT

Emollient compositions and their use to treat inflammatory skin disorders including plaque psoriasis, particularly emollient compositions comprising a combination of linoleic acid and conjugated linoleic acid.

7 Claims, 17 Drawing Sheets

EMOLLIENT COMPOSITIONS COMPRISING LINOLEIC ACID AND CONJUGATED LINOLEIC ACID AND METHODS OF USE

FIELD OF THE INVENTION

The present disclosure relates to emollient compositions and their use to treat inflammatory skin disorders including plaque psoriasis, particularly emollient compositions comprising a combination of linoleic acid and conjugated linoleic acid.

BACKGROUND

Inflammation is a complicated biological response of body tissues to damaging motivation [1] and also is a protective response connecting immune cells, blood vessels, and molecular mediators [1]. Interleukins (ILs) and tumor necrosis factor (TNF)-$\alpha$ of inflammatory cytokines are known as important biomarkers in chronic and experimental human muscle pain [2] and osteoarthritis [3]. These cytokines are produced by macrophages under inflammatory conditions [4,5]. Moreover, inflammatory macrophages potentially contribute to the enhancement of progression, metastasis, and angiogenesis of cancer cells [6, 7].

Inflammatory mouse macrophage RAW264.7 cells are of monocyte/macrophage-like cell lineage characterized by macrophage-mediated metabolic and phagocytic functions [4]. RAW264.7 cells are progressively used as modelled macrophages in inflammatory conditions in vitro. Also, RAW264.7 cells are accepted as a modelled cell for osteoclastogenesis studies [4,8]. Osteoclasts are differentiated from the monocyte-macrophage lineage [9]. Lipopolysaccharide (LPS) is a core antigen of gram-negative bacteria, which activates the innate immune system of the host [10]. LPS is an endotoxin and a persistent inflammatory stimulus to the tissue and causes osteoclastogenesis of RAW264.7 cells by regulating NF-$\kappa$B-related signaling pathways and transcriptional activity [9].

Linoleic acid, which is a polyunsaturated omega-6 fatty acid, is vital to maintain health conditions as an essential fatty acid [12]. Linoleic acid has various activities including anti-inflammatory effects, skin-lightening, acne reductive, and moisture-retentive properties when applied on the skin [13-15]. Conjugated linoleic acid, which is a family of isomers of linoleic acid, is both a trans-fatty acid and a cis-fatty acid. Conjugated linoleic acid is used as a dietary supplement for health benefits, and it may be supposed to exhibit anti-cancer benefits for prostate cancer cell proliferation [16]. Interestingly, conjugated linoleic acid may exert an anti-inflammatory effect in bovine mammary epithelial cells via the NF-$\kappa$B signaling pathway [17]. Thus, linoleic acid and conjugated linoleic acid may play a nutritional role in keeping healthy conditions. However, it is unknown how beneficial the effects of the combination of linoleic acid and conjugated linoleic acid are in the regulation of cellular function.

The study reported in example 1 has been undertaken to elucidate the effects of combinations of linoleic acid and conjugated linoleic acid on the activity of inflammatory macrophages RAW264.7 cells in vitro.

SUMMARY OF INVENTION

The Applicant has unexpectedly discovered a synergistic combination of linoleic acid and conjugated linoleic acid, having potent effects on inflammatory processes, including the inflammatory processes involved in plaque psoriasis.

Thus, in a first principal embodiment the invention provides a method of treating plaque psoriasis in a human subject in need thereof comprising topically applying to an area of skin on the subject affected by the psoriasis an emollient comprising a synergistic combination of a linoleic acid and a conjugated linoleic acid ("a LA/CLA combination"), a ceramide, and a cholesterol in an emollient base.

In a second principal embodiment the invention provides a method of treating an inflammatory skin disorder in a human subject in need thereof comprising topically applying to an area of skin on the subject affected by the disorder an emollient comprising a synergistic combination of a linoleic acid and a conjugated linoleic acid ("a LA/CLA combination"), a ceramide, and a cholesterol in an emollient base.

In a third principal embodiment the invention provides a method of treating a dry skin disorder in a human subject in need thereof comprising topically applying to an area of skin on the subject affected by the disorder an emollient comprising a synergistic combination of a linoleic acid and a conjugated linoleic acid ("a LA/CLA combination"), a ceramide, and a cholesterol in an emollient base.

In a fourth principal embodiment the invention provides an emollient composition comprising a synergistic combination of a linoleic acid and a conjugated linoleic acid ("a LA/CLA combination"), a ceramide, and a cholesterol in an emollient base.

Additional advantages of the disclosure are set forth in part in the description which follows, and in part will be obvious from the description, or may be learned by practice of the disclosure. The advantages of the disclosure will be realized and attained by means of the elements and combinations particularly pointed out in the appended claim. It is to be understood that both the foregoing general description and the following detailed description are exemplary and explanatory only and are not restrictive of the disclosure, as claimed.

BRIEF DESCRIPTION OF THE FIGURES

The accompanying drawings, which are incorporated in and constitute a part of this specification, illustrate several embodiments of the disclosure and together with the description serve to explain the principles of the disclosure.

3 of 2 replicate plates by using different cell preparations. *p<0.001 versus the control group (grey bar). 1-way ANOVA, Tukey-Kramer post-test.

Figure 3:
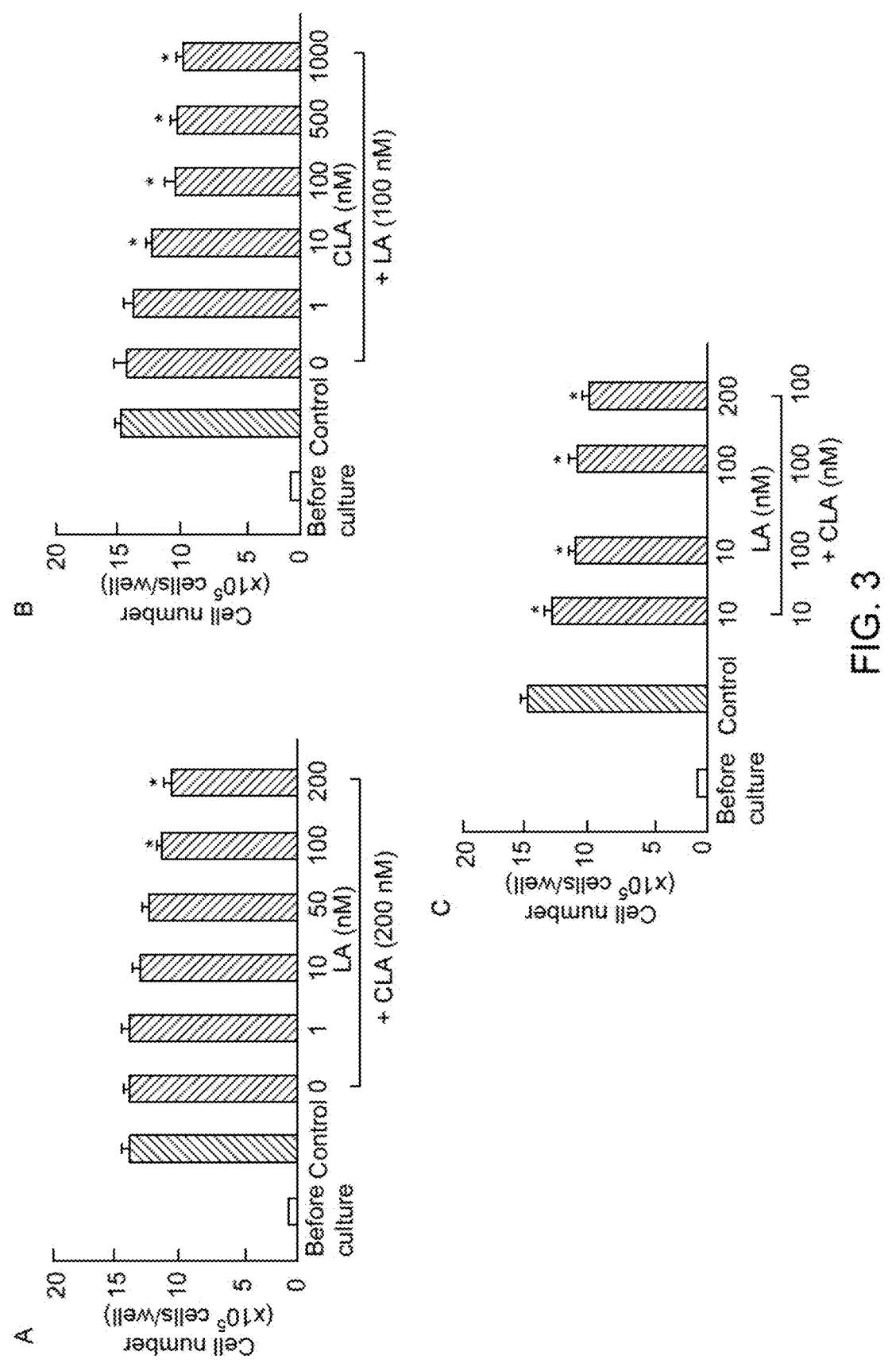

FIG. 3 depicts the effect of mixture linoleic acid and conjugated linoleic acid on the growth of mouse macrophage RAW264.7 cells in vitro. A: Cells ($1 \times 10^5$ cells/ml per well in 24-well plates) were cultured for 3 days in the presence of either vehicle (PBS) or linoleic acid (1, 10, 50, 100, or 200 nM) with or without conjugated linoleic acid (200 nM). B: Cells ($1 \times 10^5$ cells/ml per well in 24-well plates) were cultured for 3 days in the presence of either vehicle (PBS) or conjugated linoleic acid (1, 10, 100, 500, or 1000 nM) with or without linoleic acid (100 nM). C: Cells ($1 \times 10^5$ cells/ml per well in 24-well plates) were cultured for 3 days in the presence of either vehicle (PBS) or linoleic acid (10, 100, or 200 nM) with conjugated linoleic acid (10 or 100 nM). After the culture, the number of cells attached to the dish was counted. Data are presented as the mean±SD of the value obtained from 8 wells in a total of 2 replicate plates by using different cell preparations. *p<0.001 versus the control group (grey bar). 1-way ANOVA, Tukey-Kramer post-test.

Figure 4:
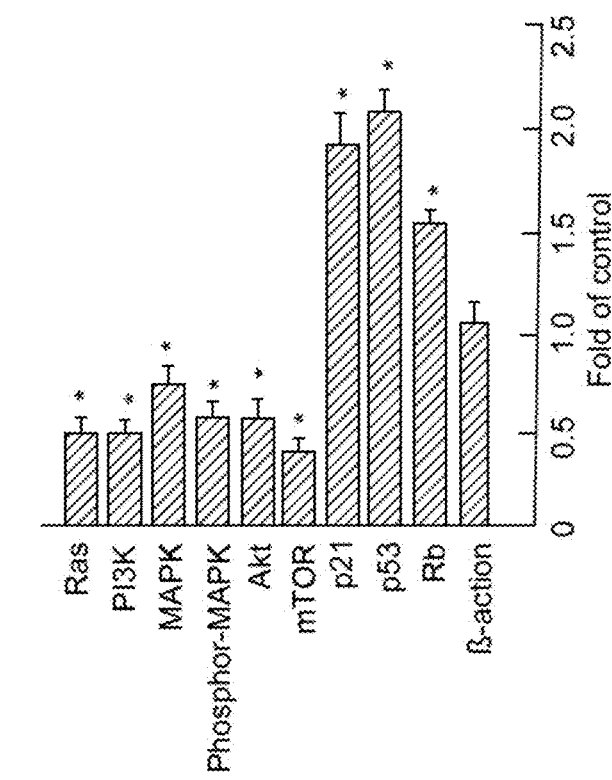
Figure 4:
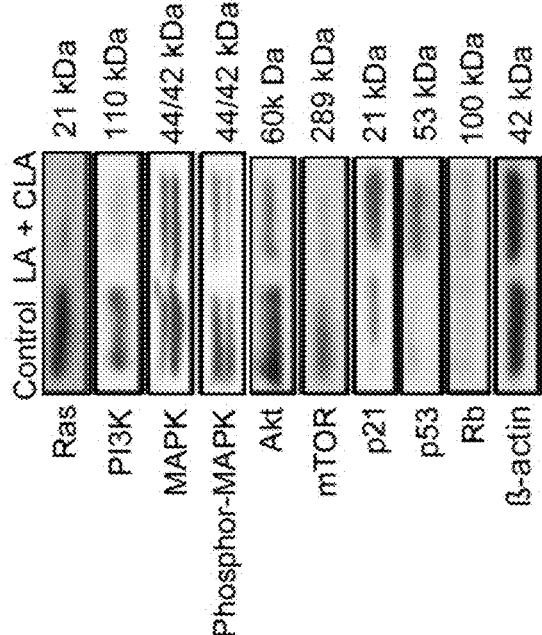

FIG. 4 depicts the effects of the combined linoleic acid (LA) and conjugated linoleic acid (CLA) on the levels of several proteins associated with proliferation of mouse macrophage RAW264.7 cells in vitro. Cells ($1 \times 10^6$ cells/10 mL of medium in 100 mm dishes) were cultured for 3 days in DMEM containing 10% FBS and 1% P/S in the presence of either vehicle (PBS) or the combined LA (100 nM) and CLA (100 nM). After culturing, the cells were removed from the dish with a cell scraper in cell lysis buffer containing protease inhibitors. Forty micrograms of supernatant protein per lane were separated by SDS-PAGE (12%) and transferred to nylon membranes for Western blotting using antibodies against various proteins. (A) Representative data are presented. (B) The band is shown as a fold of the control. Data are presented as the mean☐SD of the value obtained from 4 dishes using different cell preparations. *P<0.01 versus control. 1-way ANOVA, Tukey-Kramer post-test.

Figure 5:
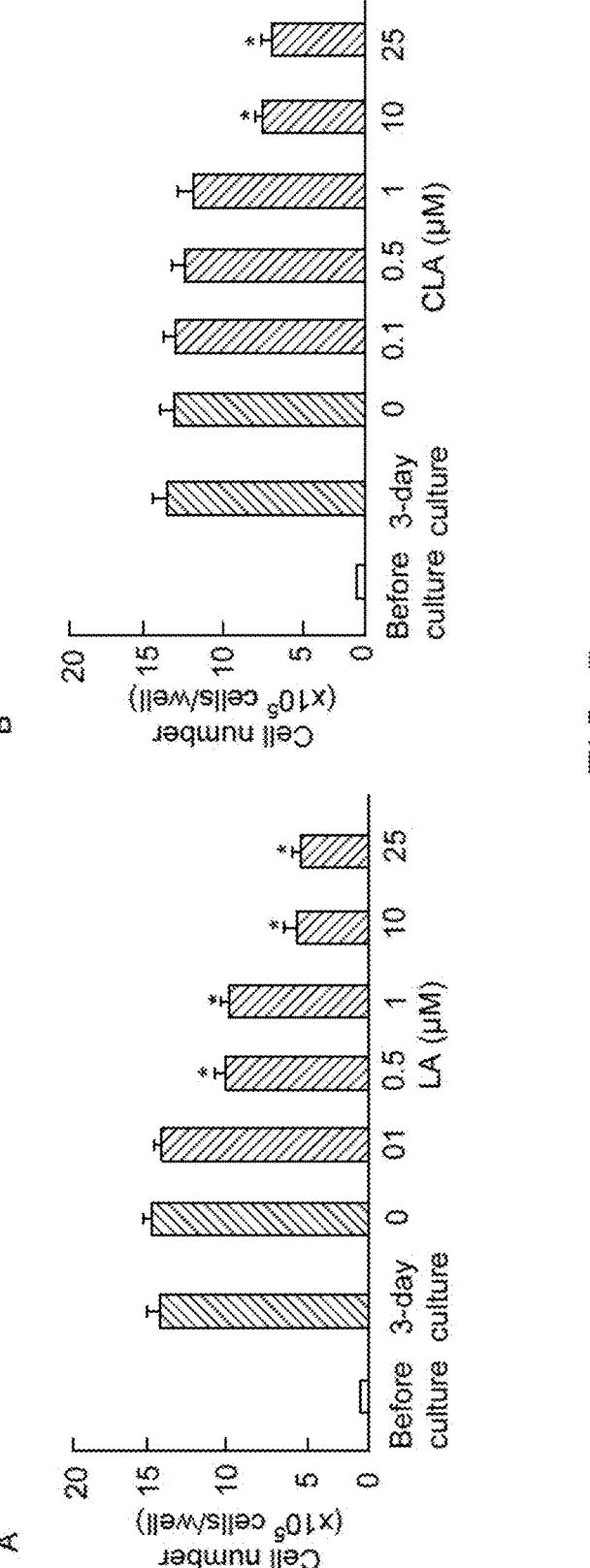

FIG. 5 depicts the effects of linoleic acid or conjugated linoleic acid on the death of mouse macrophage RAW264.7 cells in vitro. Cells ($1 \times 10^5$ cells/mL per well in 24-well plates) were cultured for 3 days, and then the cells were additionally cultured for 48 hours in the presence of either vehicle (PBS), linoleic acid (0.1, 0.5, 1, 10, or 25 μM) Figure A), or conjugated linoleic acid (0.1, 0.5, 1, 10, or 25 μM) (Figure B). After culturing, the number of cells attached to the dish was counted. Data are presented as the mean±SD of the value obtained from 8 wells in a total of 2 replicate plates by using different cell preparations. *p<0.001 versus the control group (grey bar). 1-way ANOVA, Tukey-Kramer post-test.

Figure 6:
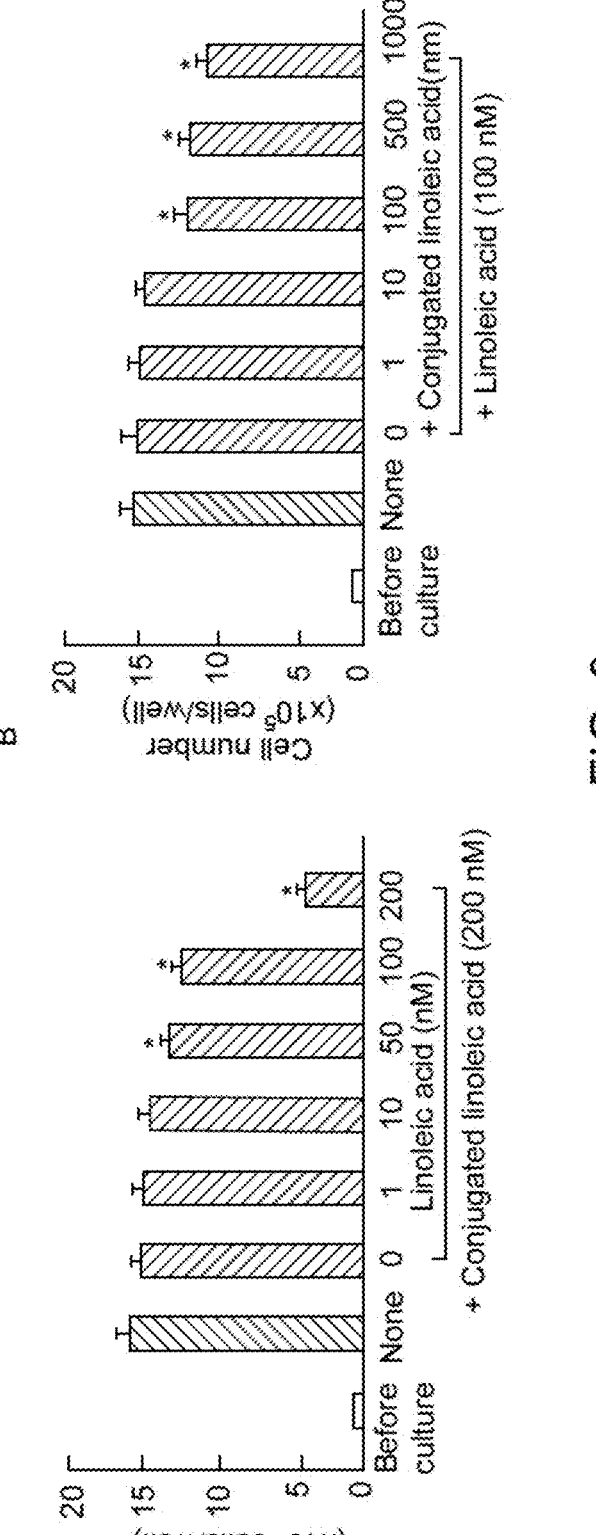
Figure 6:
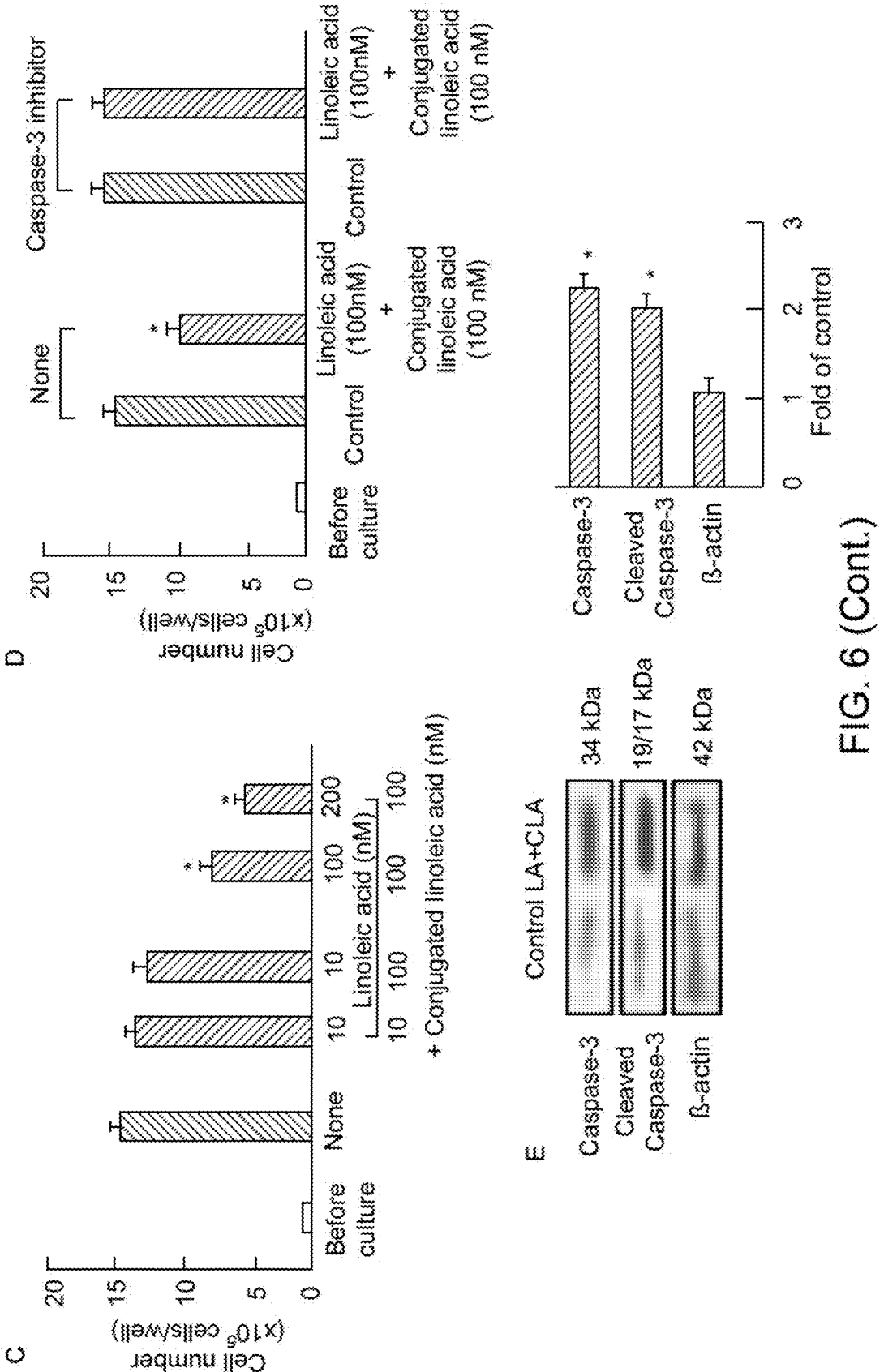

FIG. 6 depicts the effect of a mixture of linoleic acid and conjugated linoleic acid on the death of mouse macrophage RAW264.7 cells in vitro. To determine the effects of the mixture of linoleic acid and conjugated linoleic acid on the death of RAW264.7 cells, cells on reaching subconfluence with culturing for 3 days were cultured for 48 hours in DMEM (containing 10% FBS and 1% P/S) in the presence of either vehicle (PBS), linoleic acid (1, 10, 50, 100, or 200 nM) with conjugated linoleic acid (200 nM) (Figure A), or conjugated linoleic acid (1, 10, 100, 500, or 1000 M) with linoleic acid (100 nM) (Figure B). In another experiment (Figure C), subconfluent cells were cultured for 48 hours in the presence of either linoleic acid (10 nM) plus conjugated linoleic acid (10 or 100 nM) or linoleic acid (100 or 200 nM) plus conjugated linoleic acid (100 nM). In further experiments (Figure D), subconfluent cells were cultured for 48 hours in the presence of linoleic acid (100 nM) plus conjugated linoleic acid (100 nM) with or without caspase-3 inhibitor (10 μM). After incubation, the cells attached to the dish were counted. Data are presented as the mean±SD of the value obtained from 8 wells in a total of 2 replicate plates by using different cell preparations. *p<0.001 versus the control group (grey bar). 1-way ANOVA, Tukey-Kramer post-test. (E) To determine the effects of the combined linoleic acid (LA) and conjugated linoleic acid (CLA) on the levels of proteins associated with cell death in vitro, cells ($1 \times 10^6$ cells/10 mL of medium in 100 mm dishes) were cultured for 3 days in DMEM in the presence of either vehicle (PBS) or the combined LA (100 nM) and CLA (100 nM). After culturing, forty micrograms of supernatant protein per lane were separated by SDS-PAGE (12%) and transferred to nylon membranes for Western blotting. Representative data are shown. The band is shown as a fold of the control. Data are presented as the mean±SD of the value obtained from 4 dishes using different cell preparations. *p<0.01 versus control. 1-way ANOVA, Tukey-Kramer post-test.

Figure 7:
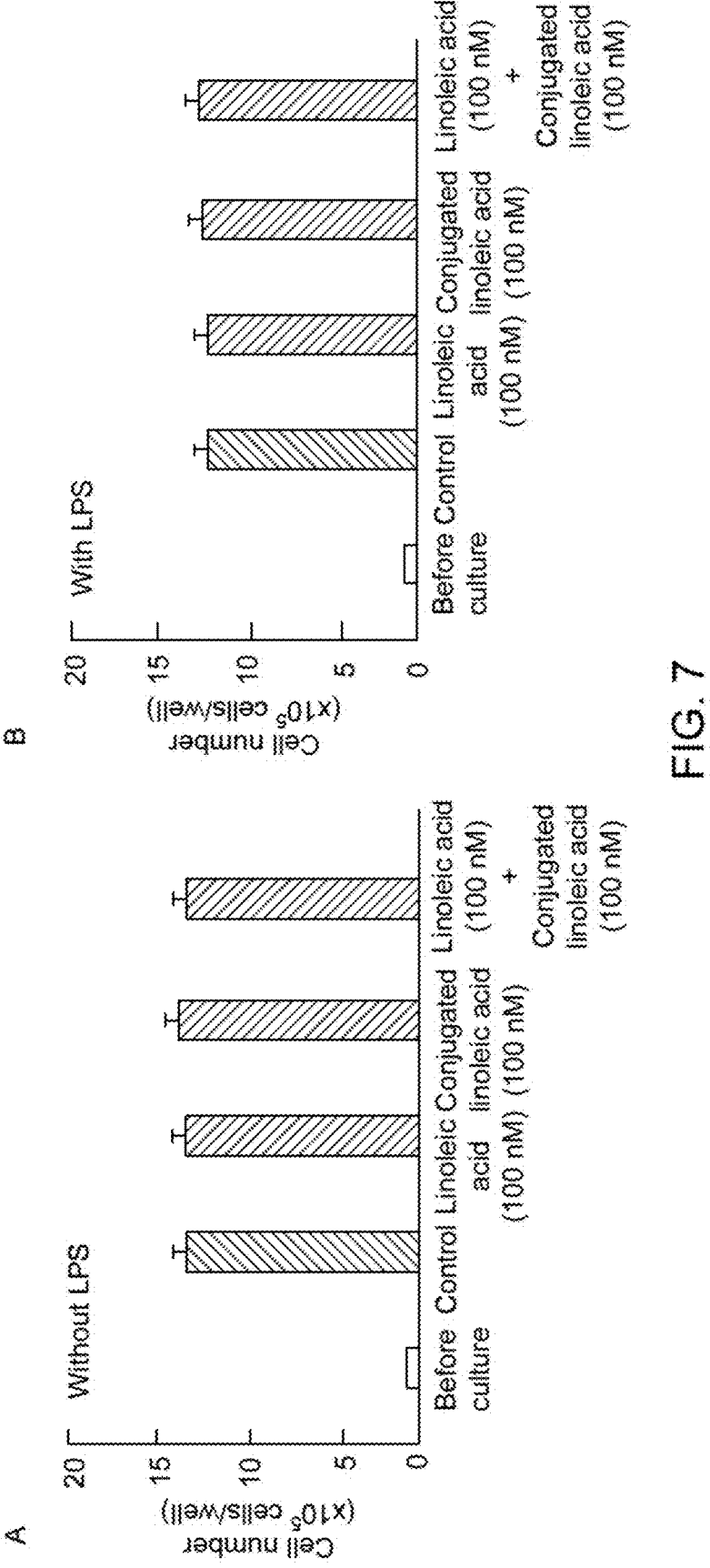

FIG. 7 depicts the effects of linoleic acid or conjugated linoleic acid in the presence of lipopolysaccharide (LPS) on the number of mouse macrophage RAW264.7 cells in vitro. Cells ($1 \times 10^5$/mL per well) were cultured using a 24-well plate in DMEM containing 10% FBS and 1% P/S for 3 days in reaching upon subconfluence, and then the cells were further cultured for 5 hours after the addition of either vehicle (PBS), linoleic acid (100 nM), conjugated linoleic acid (100 nM), or the combination of linoleic acid (100 nM) and conjugated linoleic acid (100 nM) with (Figure A) or without (Figure A) LPS (100 ng/ml). After incubation, the cells attached to the dish were counted. Data are presented as the mean±SD of the value obtained from 8 wells in a total of 2 replicate plates by using different cell preparations. Treatment groups showed no significant difference from the control group without linoleic acid (white bar). 1-way ANOVA, Tukey-Kramer post-test.

Figure 8:
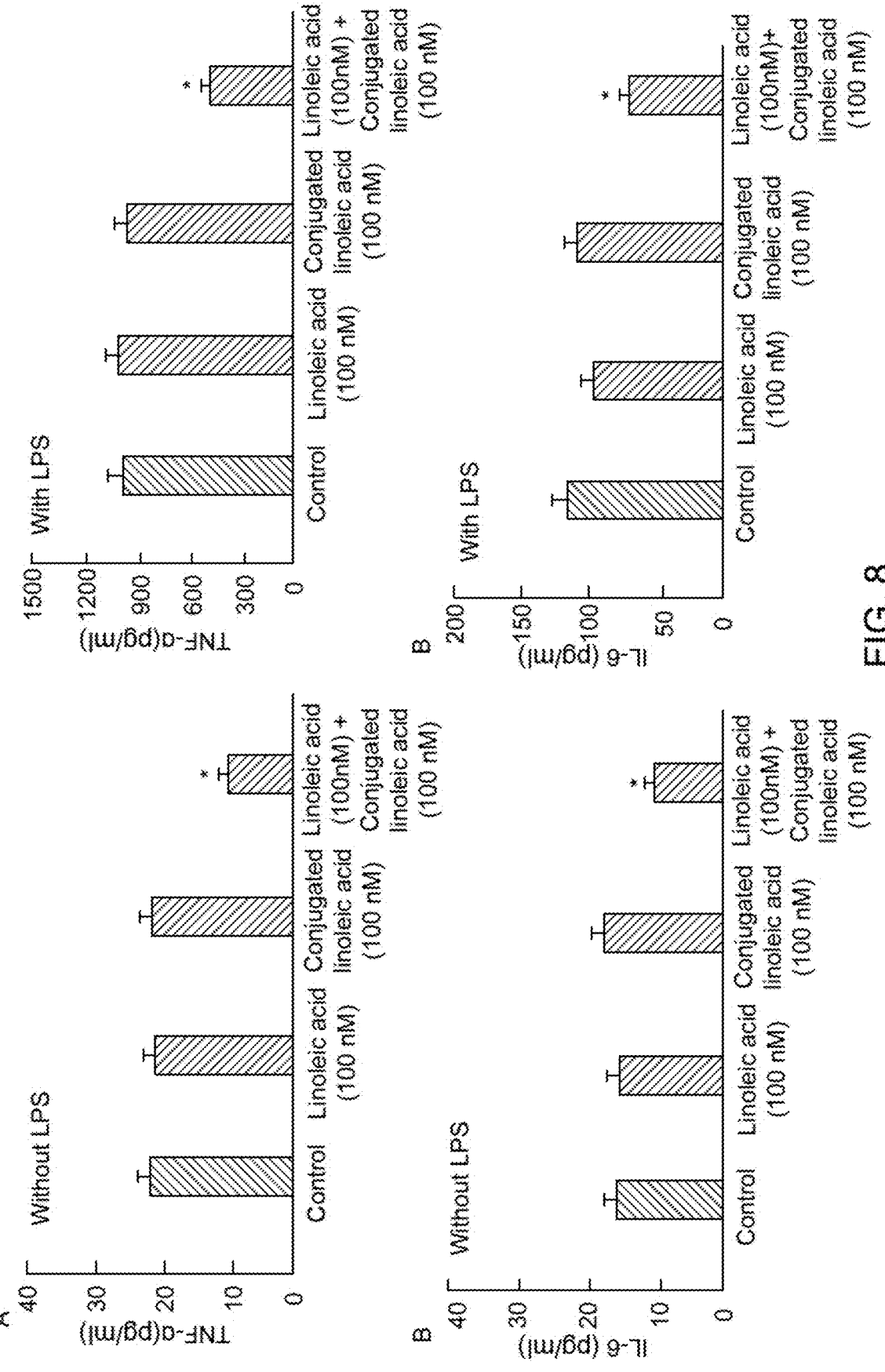
Figure 8:
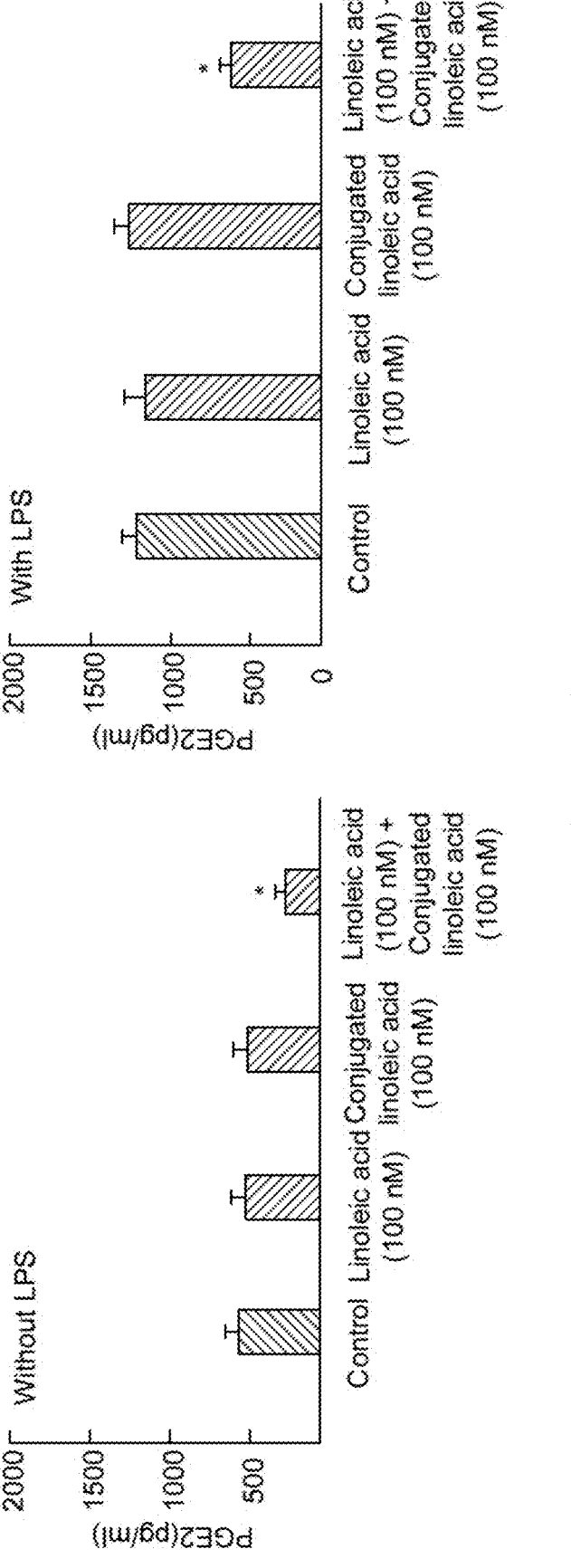

FIG. 8 depicts the effects of linoleic acid or conjugated linoleic acid on the production of cytokines from RAW264.7 cells in the presence or absence of lipopolysaccharide (LPS). Cells ($1 \times 10^5$/mL per well) were cultured using a 24-well plate in DMEM containing 10% FBS and 1% P/S for 3 days to reach subconfluence, and then the cells were further cultured for 5 hours after the addition of either vehicle (PBS), linoleic acid (100 nM), conjugated linoleic acid (100 nM), or the combination of linoleic acid (100 nM) and conjugated linoleic acid (100 nM) with or without LPS (100 ng/ml). After incubation, the medium was collected for cytokine assay. The concentrations of TNF-α (Figure A), IL-6 (Figure B), or PGE2 (Figure C) in the culture medium were determined using an ELISA kit. Data are presented as the mean±SD of the value obtained from 8 wells in a total of 2 replicate plates by using different cell preparations. *p<0.001 versus the control group without linoleic acid (white bar). 1-way ANOVA, Tukey-Kramer post-test.

Figure 9:
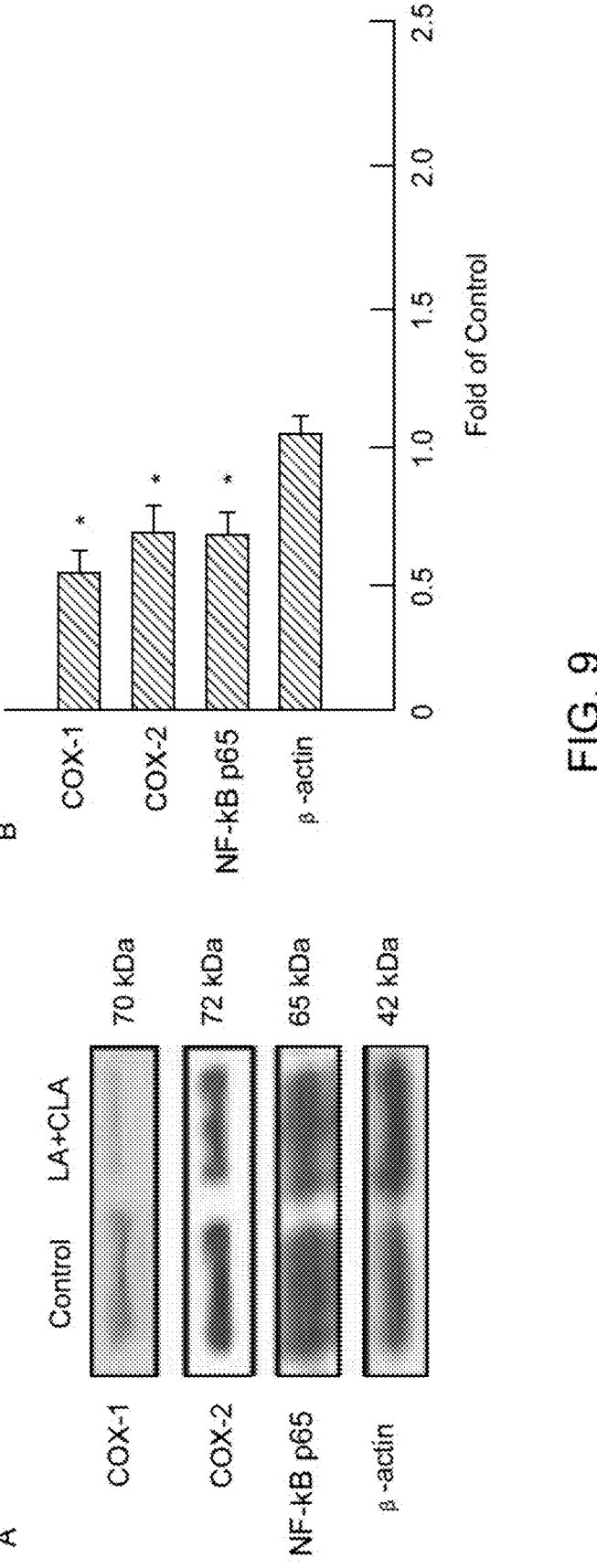

FIG. 9 depicts the effects of the combined linoleic acid (LA) and conjugated linoleic acid (CLA) on the levels of various proteins associated with cytokine production of mouse macrophage RAW264.7 cells in vitro. Cells ($1 \times 10^6$ cells/10 mL of medium in 100 mm dishes) were cultured for 3 days in DMEM containing 10% FBS and 1% P/S in the presence of either vehicle (PBS) or the combined LA (100 nM) and CLA (100 nM). After culturing, cells were removed from the dish with a cell scraper in cell lysis buffer containing protease inhibitors. Forty micrograms of supernatant protein per lane were separated by SDS-PAGE (12%) and transferred to nylon membranes for Western blotting using antibodies against COX-1, COX-2, NF-κB p65, and β-actin. (A) Representative data are shown. (B) The band was presented as a fold of the control. Data are shown as the mean±SD of the value obtained from 4 dishes using different cell preparations. *P<0.01 versus control. 1-way ANOVA, Tukey-Kramer post-test.

Figure 10:
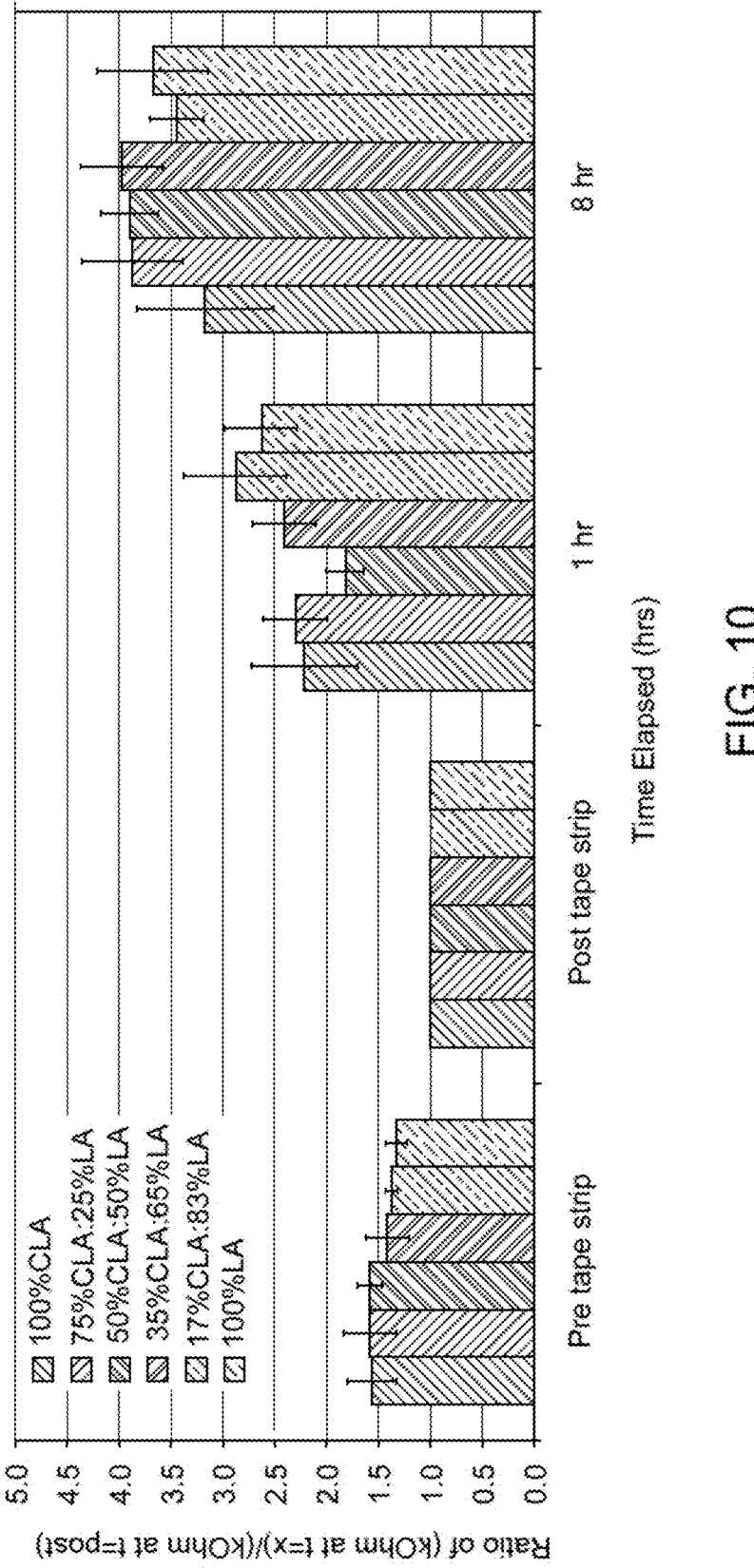

FIG. 10 a reports time lapsed TEWL results for the experiments reported in Example 2, and the various formulations tested, as kOhm ratios at various time points relative to kOhm observed at t-post.

Figure 11:
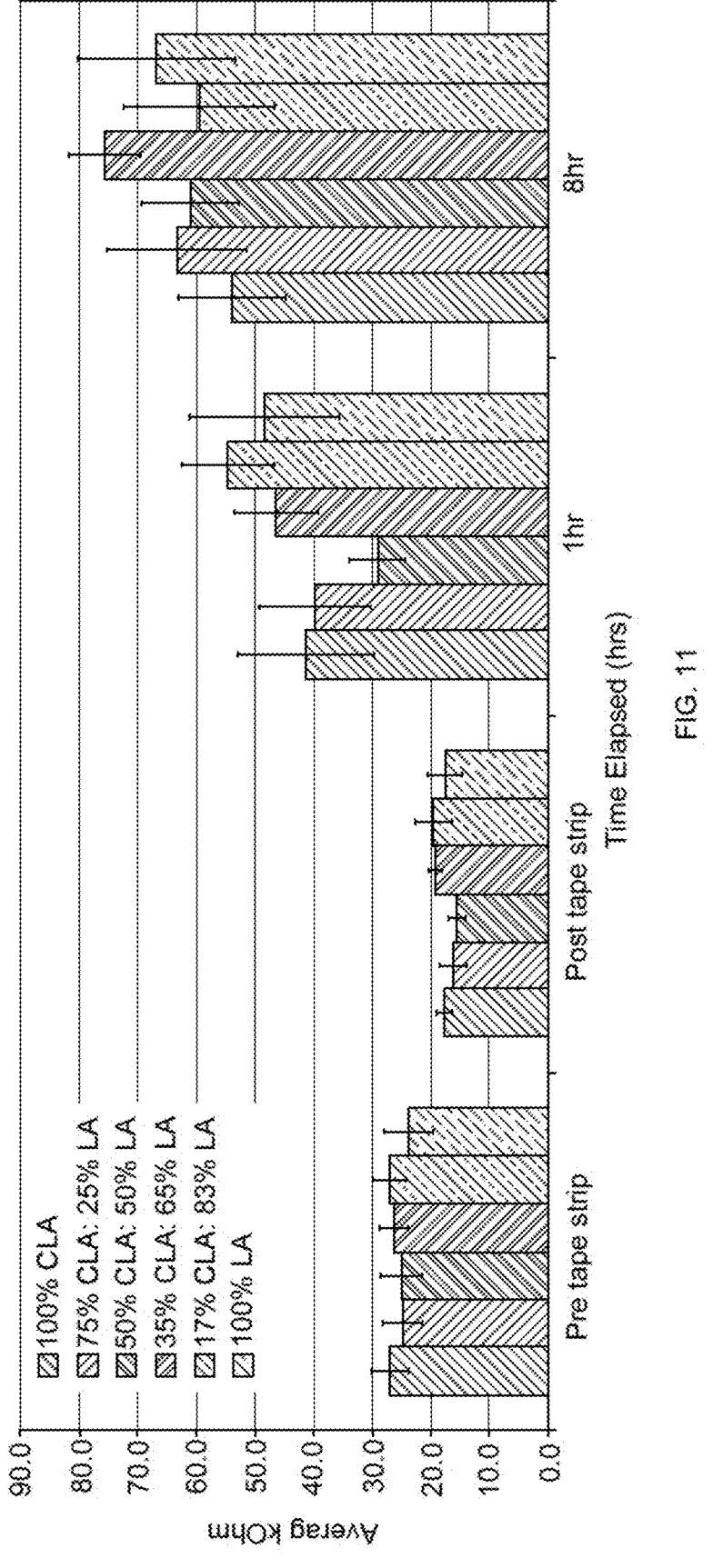

FIG. 11 a reports time lapsed TEWL results for the experiments reported in Example 2, and the various formulations tested, as average kOhm values at various time points.

Figure 12:
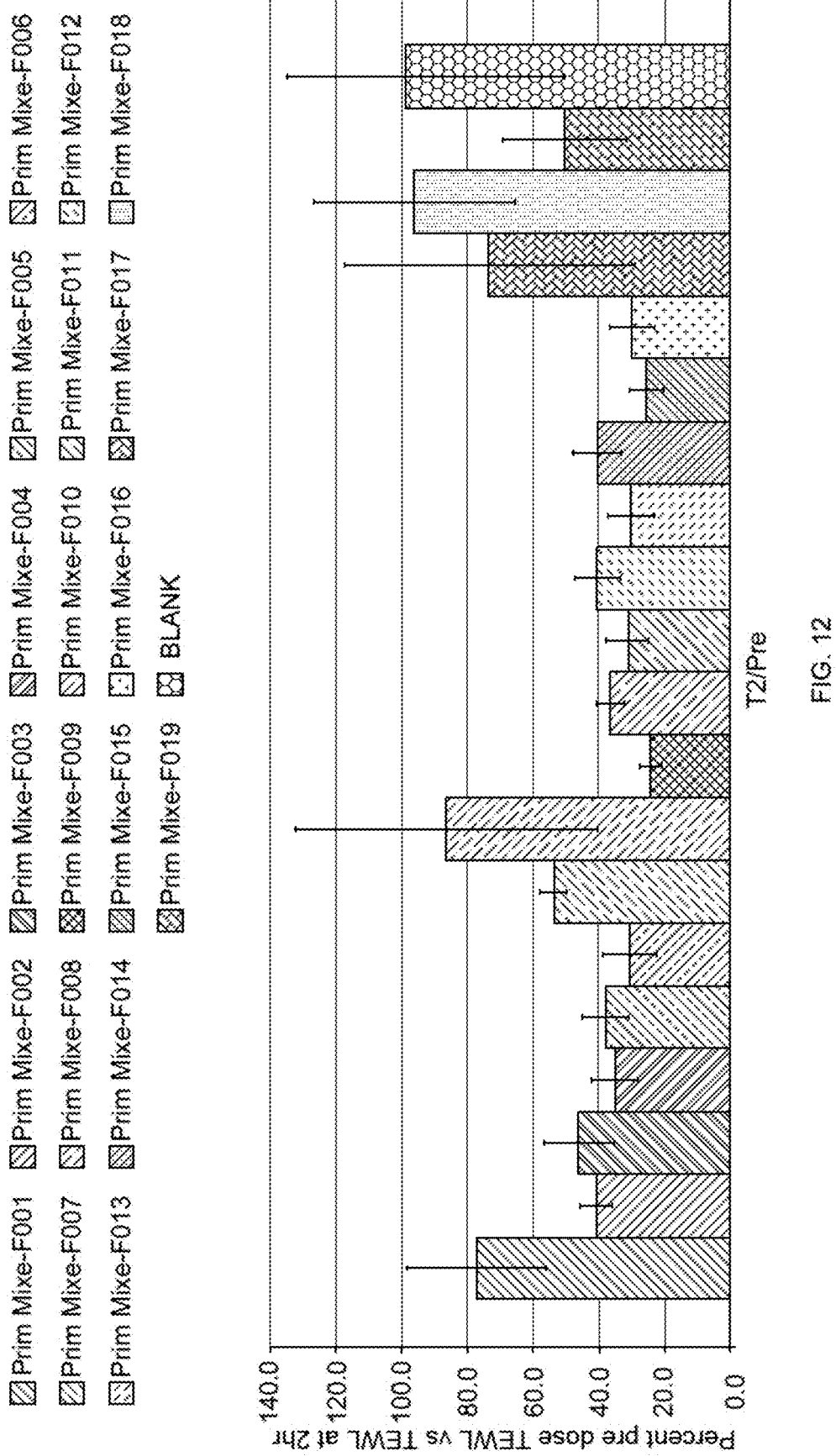

FIG. 12 reports trans-epidermal water loss (TEWL) from several formulations the ratios of LCA and CLCA, and LCA/CLCA in an emollient base, at 2 hours post-dosing, as described in Example 3.

Figure 13:
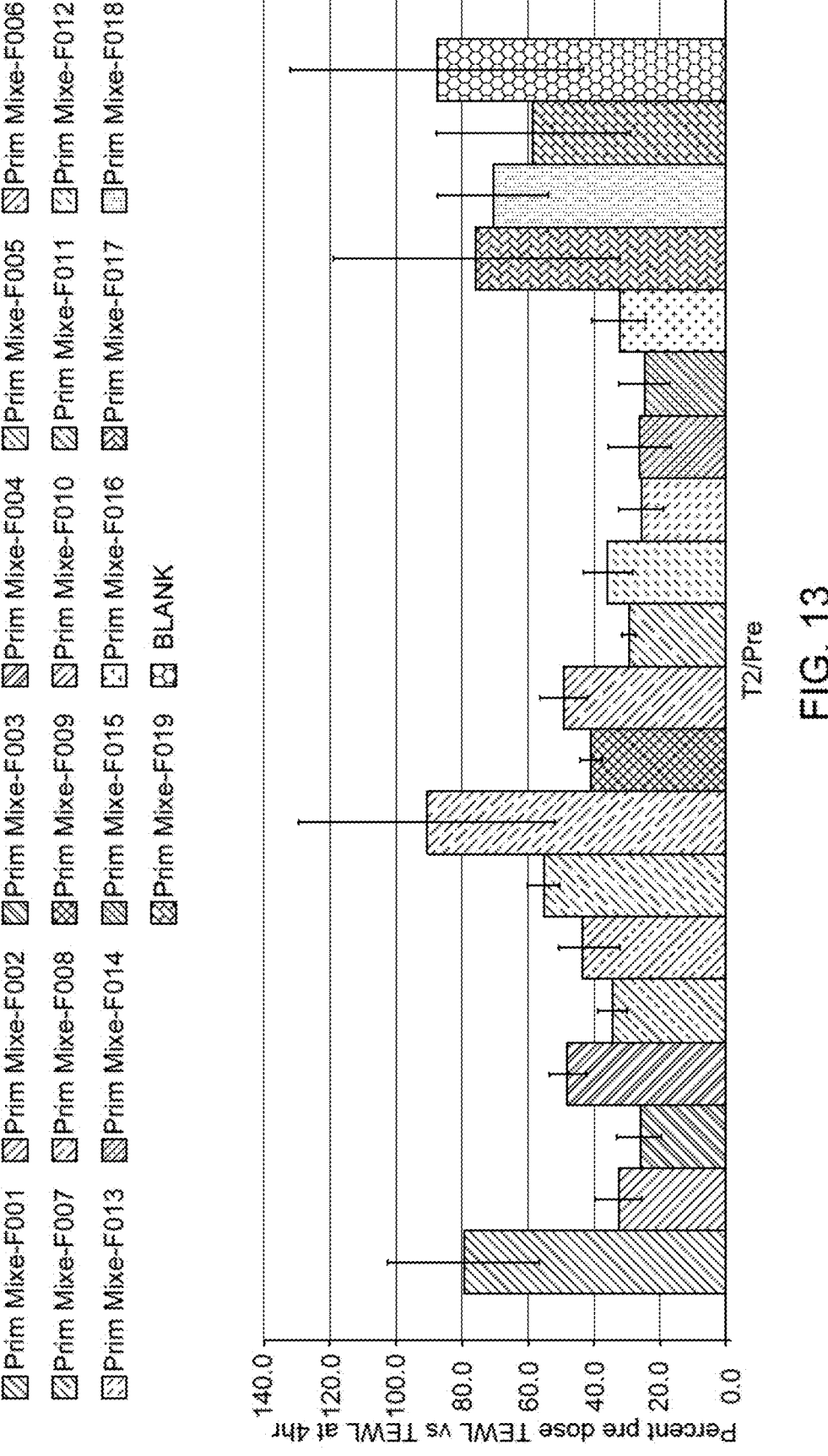

FIG. 13 reports trans-epidermal water loss (TEWL) from several formulations the ratios of LCA and CLCA, and LCA/CLCA in an emollient base, at 4 hours post-dosing, as described in Example 3.

Figure 14:
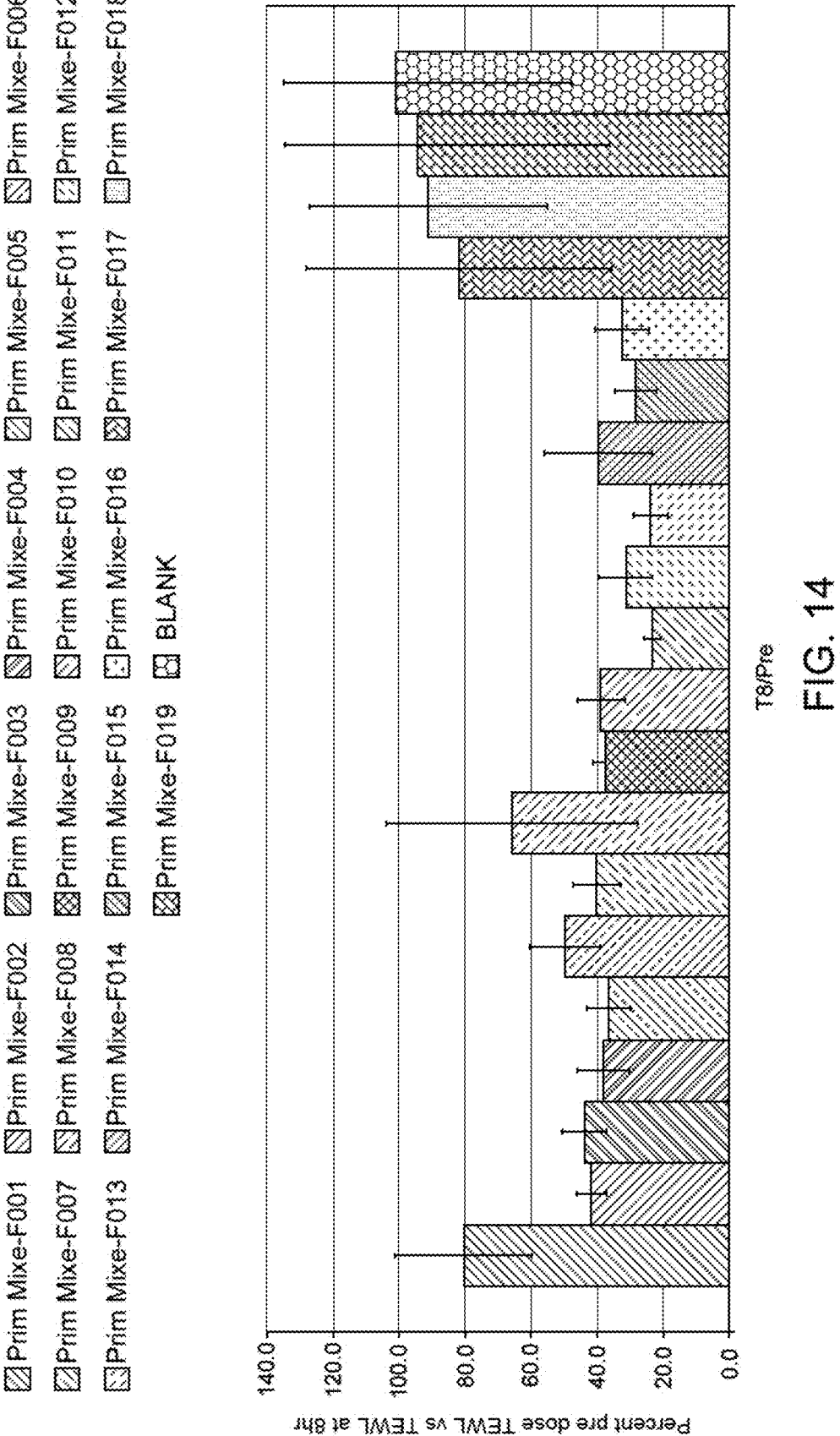

FIG. 14 reports trans-epidermal water loss (TEWL) from several formulations the ratios of LCA and CLCA, and LCA/CLCA in an emollient base, at 8 hours post-dosing, as described in Example 3.

Figure 15:
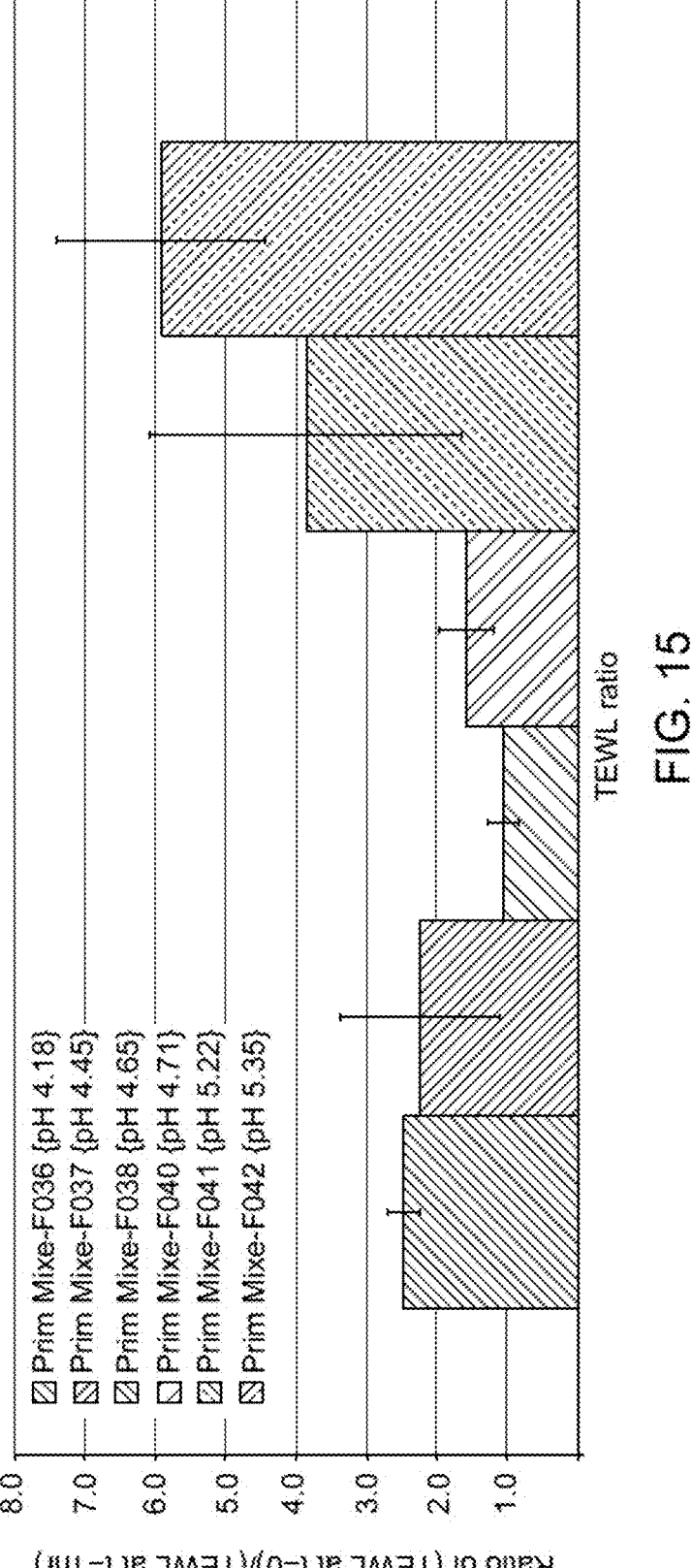

FIG. 15 reports the effect of pH on the trans-epidermal water loss from the formulations of this disclosure, as discussed in Example 3.

DETAILED DESCRIPTION

All published documents cited herein are hereby incorporated herein by reference in their entirety.
Use of Terms As used herein, the singular forms "a", "an" and "the" are intended to include the plural forms as well, unless the context clearly indicates otherwise.

Unless otherwise specified, the word "includes" (or any variation thereon, e.g., "include," "including," etc.) is intended to be open-ended. For example, "A includes 1, 2 and 3" means that A includes, but is not limited to, 1, 2 and 3.

As used in this specification and in the claim which follow, the word "comprise" and variations of the word, such as "comprising" and "comprises," means "including but not limited to," and is not intended to exclude, for example, other additives, components, integers or steps. When an element is described as comprising a plurality components, steps or conditions, it will be understood that the element can also be described as comprising any combination of such plurality, or "consisting of" or "consisting essentially of" the plurality or combination of components, steps or conditions.

When ranges are given by specifying the lower end of a range separately from the upper end of the range, or particular numerical values are specified, it will be understood that a range can be defined by selectively combining any of the lower end variables, upper end variables, and particular numerical values that is mathematically possible. When ranges are stated as extending from one endpoint to another endpoint, it will be understood that the two endpoints are included in the range. However, it will also be understood that a from/to range also includes an embodiment in which the range is defined as between the two specified endpoints, and that the term "between" can be substituted for the "from/to" language to omit the endpoints from the range. Percentages refer to weight percentages unless stated otherwise.

The present disclosure describes various embodiments. A person of ordinary skill in the art reviewing the disclosure will readily recognize that various embodiments can be combined in any variation. For example, embodiments of the disclosure include treatment of various disorders, patient populations, administrations of dosage forms, at various dosages, minimization of various adverse events, and improvements in various efficacy measures, etc. Any combinations of various embodiments are within the scope of the disclosure.

Unless defined otherwise, all technical and scientific terms used herein have the same meaning as commonly understood by one of ordinary skill in the art to which this disclosure belongs.

Definitions

"Pharmaceutically acceptable" or "physiologically acceptable" refers to compounds, salts, compositions, dosage forms and other materials which are useful in preparing a pharmaceutical composition that is suitable for veterinary or human pharmaceutical use.

As used herein, the term "pharmaceutically acceptable excipient" includes, without limitation, any binder, filler, adjuvant, carrier, excipient, glidant, sweetening agent, diluent, preservative, dye/colorant, flavor enhancer, surfactant, wetting agent, dispersing agent, suspending agent, stabilizer, isotonic agent, solvent, emulsifier, anti-caking agent, flavor, desiccants, plasticizers, disintegrants, lubricant, polymer matrix system, and polishing agents, which has been approved by or is otherwise acceptable to the United States Food and Drug Administration upon proper qualification for use in humans or domestic animals.

As used herein, the term "therapeutically effective" or "effective" refers to an amount or dose that is effective to elicit the desired biological or medical response, including the amount of a compound that, when administered to a subject for treating a disorder, is sufficient to accomplish such treatment of the disorder. The effective amount will vary depending on the disorder and its severity, and the age, weight, etc. of the subject to be treated. The effective amount may be in one or more doses (for example, a single dose or multiple doses may be required to achieve the desired treatment endpoint). An effective amount may be considered to be given in an effective amount if, in conjunction with one or more other agents, a desirable or beneficial result may be or is achieved. Suitable doses of any co-administered compounds may optionally be lowered due to the combined action, additive or synergistic, of the compound. A dose given during a "therapeutically effective period" is by definition a "therapeutically effective amount."

As used herein, the terms "treatment," "treat," and "treating" refer to reversing, alleviating, delaying the onset of, or inhibiting the progress of a disease or disorder, or one or more symptoms thereof, including but not limited to therapeutic benefit. In some embodiments, treatment is administered after one or more symptoms have developed, for example, acute exacerbation of symptoms. In some embodiments, treatment may be administered in the absence of symptoms. For example, treatment may be administered to a subject prior to the onset of symptoms (e.g., in light of a history of symptoms and/or in light of genetic or other susceptibility factors). Treatment may also be continued after symptoms have resolved, for example to prevent or delay their recurrence.

The term "linoleic acid" refers to an organic compound with the formula $HOOC(CH_2)_7CH{=}CHCH_2CH{=}CH$ $(CH_2)_4CH_3$. Both alkene groups are cis. It is a fatty acid sometimes denoted 18:2 (n-6) or 18:2 cis-9,12. Linoleic acid is a polyunsaturated omega-6 fatty acid. It is a colorless liquid that is virtually insoluble in water but soluble in many organic solvents. It typically occurs in nature as a triglyceride (ester of glycerin) rather than as a free fatty acid. It is one of two essential fatty acids for humans, who must obtain it through their diet, and the most essential, because the body uses it as a base to make the others.

The term "conjugated linoleic acid" refers to a family of isomers of linoleic acid. An example is rumenic acid. In principle, 28 isomers are possible. CLA is found mostly in the meat and dairy products derived from ruminants. The two C=C double bonds are conjugated (i.e., separated by a single bond). CLAs can be either cis-fats or trans-fats. A preferred conjugated linoleic acid is a mixture of conjugated cis-9, trans-11 linoleic acid and conjugated trans-10, cis-12 linoleic acid, preferably a 1:1 molar ratio, which is the same combination tested in Example 1.

The term "synergistic" combination of conjugated linoleic acid and linoleic acid refers to any combination of linoleic acid and conjugated linoleic acid. In one embodiment the term refers to any combination of linoleic acid and conjugated linoleic acid, at a ratio which has been shown to exhibit synergy in the examples of this document, +/−20%, 10%, 5%, 3%, or 1%. In one embodiment, the term refers to a 1:1 weight or molar ratio of linoleic acid to conjugated linoleic acid +/−20%, 10%, 5%, 3%, or 1%. In another embodiment, the term refers to a 1:1 weight or molar ratio of linoleic acid to conjugated linoleic acid +/−20%, 10%, 5%, 3%, or 1%, in an emollient in which the combination of linoleic acid to conjugated linoleic acid is present in an amount of from 0.1 to 2.5 wt. %, or from 0.2 to 1 wt. %, or about 0.53 wt %.

Discussion

In a first principal embodiment the invention provides a method of treating plaque psoriasis in a human subject in need thereof comprising topically applying to an area of skin on the subject affected by the psoriasis an emollient comprising a synergistic combination of a linoleic acid and a conjugated linoleic acid ("a LA/CLA combination"), a ceramide, and cholesterol in an emollient base.

In a second principal embodiment the invention provides a method of treating an inflammatory skin disorder in a human subject in need thereof comprising topically applying to an area of skin on the subject affected by the disorder an emollient comprising a synergistic combination of a linoleic acid and a conjugated linoleic acid ("a LA/CLA combination"), a ceramide, and a cholesterol in an emollient base.

In a third principal embodiment the invention provides a method of treating a dry skin disorder in a human subject in need thereof comprising topically applying to an area of skin on the subject affected by the disorder an emollient comprising a synergistic combination of a linoleic acid and a conjugated linoleic acid ("a LA/CLA combination"), a ceramide, and a cholesterol in an emollient base.

Suitable dry skin conditions include, but are not limited to, dry skin, psoriasis, sjogrens, ichthyosis, scleroderma, ichthyosis vulgaris, dry skin with autoimmune diseases, and lupus.

In a fourth principal embodiment the invention provides an emollient composition comprising a synergistic combination of a linoleic acid and a conjugated linoleic acid ("a LA/CLA combination"), a ceramide, and a cholesterol in an emollient base.

In another embodiment the emollient is applied to the area twice daily for up to 14 days.

The weight ratio of linoleic acid to conjugated linoleic acid can fall within various ranges, but generally falls within the synergistic ratios described in the Examples hereto. Thus, the weight ratio of linoleic acid to conjugated linoleic acid generally falls within the range of about 5:1 to 1:5, 4:1 to 1:4; 3:1 to 1:3; 2:1 to 1:2, 1:1 to 2:1, 1:1 to 3:1, 1:3 to 1:1, 1:2 to 1:1, or 1:1.

In another embodiment, the emollient comprises from about 0.1 to 2.5 wt % of the combination of CLA and LA, from about 0.2 to 1 wt % of the combination of CLA and LA, or about 0.53 wt % of the combination of CLA and LA.

In another embodiment the emollient comprises the ceramide, the LA/CLA combination, and the cholesterol in a physiologically balanced ratio, preferably of 3:1:1+/−10%, 5%, 3%, or 1% (e.g., the amounts of the LA/CLA combination and cholesterol can each vary from the amount of ceramide in the formulation by the recited percentage; the amount of ceramide can vary from the amount of cholesterol in the recited percentage, etc.). A physiologically balanced ratio generally refers to 3:1:1 and substantial equivalents thereof. The relative percentages of the three components can in one embodiment vary by as much as 20%.

In another embodiment the emollient comprises from 50-75% water and 25-50% of an emollient base (defined as the ingredients which cause the formation of an emollient such as petrolatum and dimethicone and xanthan gum, in addition to any active ingredients such as the combination of the ceramide, the linoleic acid, the conjugated linoleic acid, and the cholesterol). In another embodiment, the emollient comprises from 1-10% of the combination of the ceramide, the conjugated linoleic acid, and the cholesterol. In another embodiment, the emollient comprises from 1-5% of the combination of the ceramide, the conjugated linoleic acid, and the cholesterol.

In another embodiment the emollient has a pH of 5+/−10% or 5%.

In another embodiment the emollient has a pH of from 4.2 to 4.85.

In another embodiment the emollient has a pH of from 4.5 to 4.8.

In another embodiment the emollient has a pH of from 4.6 to 4.75.

In another embodiment the emollient is an emulsion comprising or consisting essentially of water, lipids, glyceryl stearate, squalene, glycerin, PEG-100 stearate, hydroxypropyl bispalmitamide (ceramide), petrolatum, dimethicone, phenoxyethanol, cholesterol, conjugated linoleic acid, citric acid, palmitic acid, xanthan gum, potassium hydroxide, disodium EDTA, sorbic acid, and capric acid, and functionally equivalent substitutable ingredients.

EXAMPLES

In the following examples, efforts have been made to ensure accuracy with respect to numbers (e.g., amounts, temperature, etc.) but some errors and deviations should be accounted for. The following examples are put forth so as to provide those of ordinary skill in the art with a complete disclosure and description of how the methods claimed herein are made and evaluated and are intended to be purely exemplary of the disclosure and are not intended to limit the scope of what the inventors regard as their invention.

Example 1. Evaluation of Linoleic Acid and Conjugated Linoleic Acid Combinations on the Growth and Death of Inflammatory Macrophages RAW264.7 Cells In Vitro This study was undertaken to evaluate the effect of linoleic acid and conjugated linoleic acid, both individually and in combination, on an accepted model of inflammatory processes.

Materials and Methods

Reagents

Dulbecco's Modification of Eagle's Medium (DMEM) with 4.5 g/L glucose, L-glutamine and sodium pyruvate and antibiotics (100 units/mL penicillin and 100 μg/mL streptomycin; 1% P/S) was obtained from Corning (Mediatech, Inc. Manassas, VA, USA). Fetal bovine serum (FBS) was purchased from Hyclone (Logan, UT, USA). Linoleic acid, conjugated linoleic acid, and all other reagents were purchased from Sigma-Aldrich (St. Louis, MO, USA) unless otherwise specified. These reagents was diluted in sterile phosphate-buffered saline (PBS).

RAW264.7 Cells

RAW264.7 cells are monocyte/macrophage-like cell lineage, originating from Abelson leukemia virus-transformed cell lineages derived from BALB/c mice. Mouse macrophage RAW264.7 cells were obtained from the American Type Culture Collection (Rockville, MD, USA). RAW264.7 cells were cultured in DMEM containing 10% FBS, and 1% P/S.

Assay of Cell Growth

To determine the effects of linoleic acid and conjugated linoleic acid on cell growth, RAW264.7 cells ($1 \times 10^5$/ml per well in 24-well plates) were cultured in DMEM containing 10% FBS and 1% P/S. Cells were cultured in DMEM and either vehicle (phosphate-buffered saline, PBS) or linoleic acid or conjugated linoleic acid (10 μM) for 1, 2, 3, or 4 days in a water-saturated atmosphere containing 5% $CO_2$ and 95% air at 37° C. In separate experiments, to investigate the effects of increasing concentrations of linoleic acid or conjugated linoleic acid on the growth of RAW264.7 cells, the cells ($1 \times 10^5$/ml per well) were cultured in DMEM (containing 10% FBS and 1% P/S) in the presence of either vehicle (PBS), linoleic acid, or conjugated linoleic acid (0.1-25 μM) for 3 days. In another experiment, to elucidate the effects of the mixture of linoleic acid and conjugated linoleic acid on the growth of RAW264.7 cells, cells were cultured in DMEM (containing 10% FBS and 1% P/S) in the presence of either vehicle (PBS), linoleic acid (1-200 nM), or conjugated linoleic acid (1-1000 M) with or without conjugated linoleic acid (200 nM) or linoleic acid (100 nM) for 3 days.

Cell Counting

After culture, the cells were detached from each well by adding a sterile solution (0.1 ml per well) of 0.05% trypsin plus EDTA in $Ca^{2+}$/$Mg^{2+}$-free PBS (Thermo Fisher Scientific, Waltham, MA, USA) with incubation for 2 min at 37° C. 0.9 ml of DMEM containing 10% FBS, and 1% P/S was then added to each well. To determine the number of cells, the medium containing the suspended cells (0.1 ml) was mixed with 0.1 ml of 0.5% trypan blue staining solution, which can differentiate between living cells and dead cells. Viable cells were counted under a microscope (Olympus MTV-3) with a Hemocytometer (Sigma-Aldrich, St. Louis, MO) using a cell counter (Line Seiki H-102P, Tokyo, Japan). For each dish, we took the average of two counts. Cell numbers were shown as numbers per well.

Statistical Analysis

Statistical significance was estimated using GraphPad InStat version 3 for Windows XP (GraphPad Software Inc. La Jolla, CA). Data are presented as the mean±standard deviation (SD). We used Student-t-test to calculate the statistical significance between the 2 groups. As indicated, Multiple comparisons were performed by one-way analysis of variance (ANOVA) with Tukey-Kramer multiple comparisons post-test for the parametric data. A p-value of <0.05 was considered statistically significant.

Results

Figure 1:
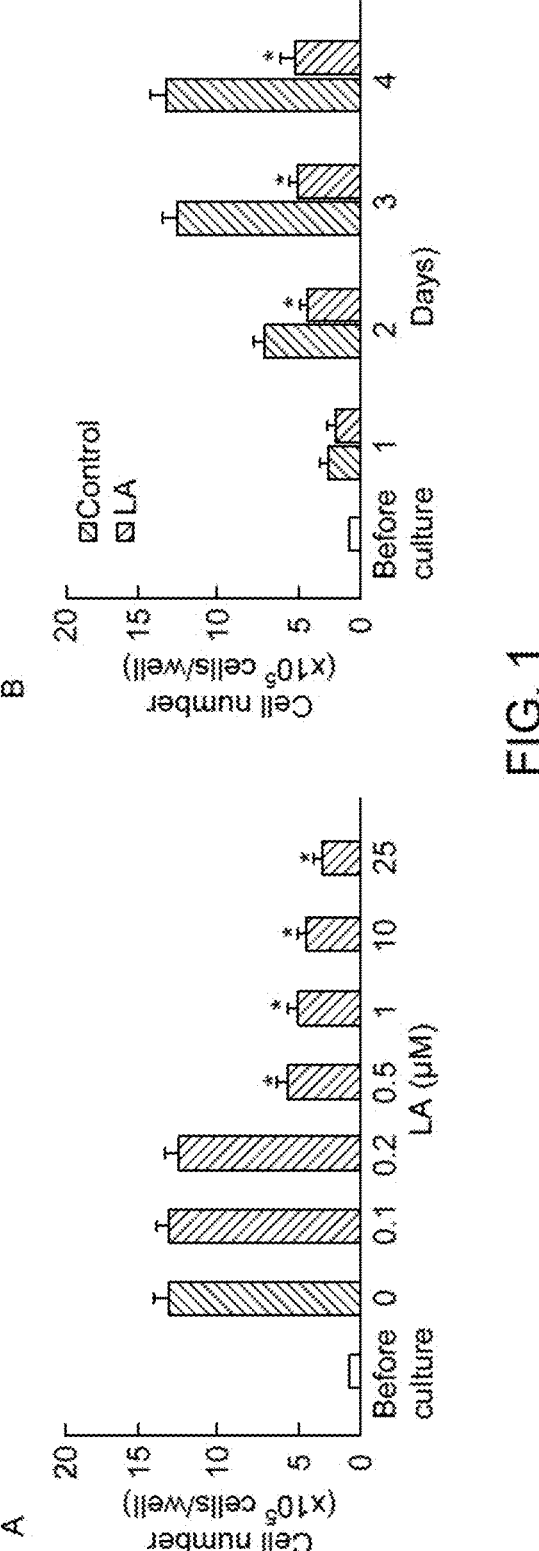
FIG. 1 depicts the effects of linoleic acid on the growth of mouse macrophage RAW264.7 cells in vitro. A: Cells ($1\times10^5$ cells/ml per well in 24-well plates) were cultured for 1, 2, 3, or 4 days in the presence of either vehicle (PBS) or linoleic acid (10 $\mu$M). B: Cells ($1\times10^5$ cells/ml per well in 24-well plates) were cultured for 3 days in the presence of either vehicle (PBS) or linoleic acid (0.1, 0.5, 1, 10, or 25 $\mu$M). After the culture, the number of cells attached to the dish was counted. Data are presented as the mean±SD of the value obtained from 8 wells in a total of 2 replicate plates by using different cell preparations. *p<0.001 versus the control group (grey bar). 1-way ANOVA, Tukey-Kramer post-test.
Figure 2:
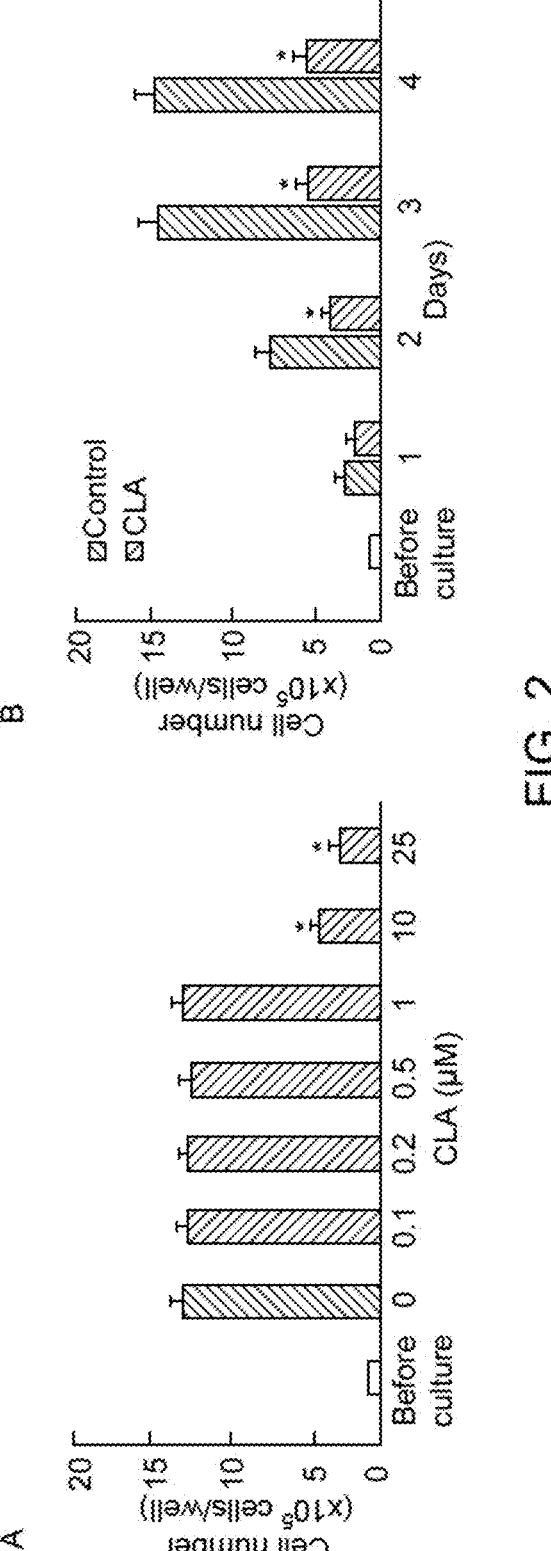
FIG. 2 depicts the effects of conjugated linoleic acid on the growth of mouse macrophage RAW264.7 cells in vitro. A: Cells ($1\times10^5$ cells/ml per well in 24-well plates) were cultured for 1, 2, 3, or 4 days in the presence of either vehicle (PBS) or conjugated linoleic acid (10 $\mu$M). B: Cells ($1\times10^5$ cells/ml per well in 24-well plates) were cultured for 3 days in the presence of either vehicle (PBS) or conjugated linoleic acid (0.1, 0.5, 1, 10, or 25 $\mu$M). After the culture, the number of cells attached to the dish was counted. Data are presented as the mean±SD of the value obtained from 8 wells in a total

First, we investigated whether linoleic acid or conjugated linoleic acid impacts the growth of mouse macrophage RAW264.7 cells. Cells were cultured for 1, 2, 3, and 4 days in the presence of either vehicle (PBS), linoleic acid (10 μM) (FIG. 1A), or conjugated linoleic acid (10 μM) (FIG. 2A). Cell growth was repressed by culturing with linoleic acid or conjugated linoleic acid at 10 UM for 2-4 days. Next, we determined the effects on cell growth of increasing concentrations of linoleic acid (0.1-25 μM) (FIG. 1B) or conjugated linoleic acid (0.1-25 μM) (FIG. 2B) with culturing for 3 days. Cell growth was repressed by linoleic acid at concentrations of 0.5-25 μM (FIG. 1B) and conjugated linoleic acid at concentrations of 10 and 25 μM (FIG. 2B).

We next investigated whether the combination of linoleic acid or conjugated linoleic acid expressed a synergistic effect on the growth of RAW264.7 cells in vitro. In one set of experiments, cells were cultured for 3 days in DMEM containing either vehicle (PBS) or linoleic acid (1-200 nM) with conjugated linoleic acid (200 nM) (FIG. 3A). 200 nM conjugated linoleic acid caused a significant repressive effect on cell growth in the presence of linoleic acid (100 and 200 nM) (FIG. 3A) even though none of 200 nM linoleic acid, 100 nM conjugated linoleic acid, or 200 nM conjugated linoleic acid individually suppressed cell growth.

In another set of experiments, cells were cultured for 3 days in DMEM containing either vehicle (PBS) or conjugated linoleic acid (1-1000 nM) with linoleic acid (100 nM) (FIG. 3B). Consistent with the first set of experiments, the combination of conjugated linoleic acid (10-1000 nM) with linoleic acid (100 nM) significantly suppressed cell growth (FIG. 3B), even though none of 100 nM linoleic acid, 100 nM conjugated linoleic acid, or 200 nM conjugated linoleic acid individually repressed cell growth. Culturing of linoleic acid (100 or 200 nM) with conjugated linoleic acid (100 nM) also significantly repressed cell growth (FIG. 3C).

Mechanistically, it was investigated whether the expression levels of various proteins associated with the regulation of proliferation of RAW264.7 cells in vitro are altered by culturing with the combined linoleic acid and conjugated linoleic acid in RAW264.7 cells (FIG. 4). Culturing with the combined linoleic acid (100 nM) and conjugated linoleic acid (100 nM), which have a suppressive effect on cell growth, decreased the levels of Ras, PI3K, MAPK, phosphorylated MAPK, and mTOR, which are associated with promoting cell proliferation. In addition, their mixture caused an increase in the levels of p21, p53 and Rb, which are involved in cell repression. These results suggest that the combined linoleic acid and conjugated linoleic acid exert potent suppressive effects on the growth of macrophage RAW264.7 cells in vitro via regulation of different signaling pathways.

Furthermore, it was elucidated whether linoleic acid or conjugated linoleic acid affects the death of macrophage RAW264.7 cells in vitro. Cells were cultured for 3 days on reaching subconfluence, and then they were additionally cultured for 48 hours in the presence of either vehicle (PBS), linoleic acid (0.1, 0.5, 1, 10, or 25 μM), or conjugated linoleic acid (FIG. 5B). The death of RAW264.7 cells was stimulated by culturing with linoleic acid (0.5, 1, 10, or 25 μM) (FIG. 5A) or conjugated linoleic acid (10 or 25 μM) (FIG. 5B).

We then examined the combined effects of linoleic acid (1, 10, 50, 100, or 200 nM) or conjugated linoleic acid (1, 10, 100, 500, or 1000 nM) at comparatively lower concentrations on the death of RAW264.7 cells in vitro (FIG. 6). Cells that reached subconfluence after 3 days of culture were additionally cultured for 48 hours in the presence of linoleic acid (1, 10, 50, 100, or 200 nM) with conjugated linoleic acid (1, 10, 100, 500, or 1000 nM) (FIG. 6A). Culturing with linoleic acid (50, 100, or 200 nM), which had no significant suppressive effect on cell death, caused a significant stimulatory effect on cell death in the presence of conjugated linoleic acid (200 nM), which had no significant effect on cell growth (FIG. 5). Similarly, the mixture of conjugated linoleic acid (100, 500, or 1000 nM) with linoleic acid (100 nM), which did not have a stimulatory effect on cell death as shown in FIG. 5, expressed a significant stimulatory effect on cell death (FIG. 6B). Also, culture with linoleic acid (100 or 200 nM) with conjugated linoleic acid (100 nM) caused a significant stimulatory effect on cell death (FIG. 6C), although the mixture with linoleic acid (10 nM) and conjugated linoleic acid (10 or 100 nM) did not have a significant effect on cell growth. These results support the view that the composition of linoleic acid and conjugated linoleic acid with a lower concentration expresses a potent synergistic effect in stimulating the death of macrophage RAW264.7 cells in vitro.

Mechanistically, we found that the stimulatory effects of combined linoleic acid (100 nM) and conjugated linoleic acid (100 nM) on RAW264.7 cell death in vitro were blocked by the presence of caspase-3 inhibitor (FIG. 6D), suggesting promotion of apoptotic cell death. Furthermore, the combination of linoleic acid (100 nM) and conjugated linoleic acid (100 nM) was shown to increase the levels of caspase-3 and cleaved caspase-3 in RAW264.7 cells in vitro (FIG. 6E), which are associated with the induction of apoptotic cell death.

We also determined whether linoleic acid and conjugated linoleic acid at a comparatively lower concentration (100 nM) affected the number of RAW264.7 cells in vitro in the presence of LPS (100 ng/mL) (FIG. 7). RAW264.7 cells grown to subconfluence for 3 days were additionally cultured for 5 hours in the presence of linoleic acid (100 nM), conjugated linoleic acid (100 nM), or combined linoleic acid (100 nM) and conjugated linoleic acid (100 nM) with or without LPS. The number of RAW264.7 cells was not altered by the addition of these compounds (FIG. 7).

The levels of TNF-α (FIG. 8A), IL-6 (FIG. 8B), or PGE2 (FIG. 8C) in the culture medium cultured for 5 hours in the presence of linoleic acid and conjugated linoleic acid without LPS were decreased by the addition of combined linoleic acid (100 nM) and conjugated linoleic acid (100 nM), while these cytokine productions were not affected by the addition of either chemical. Culturing with LPS caused a remarkable increase in cytokine production. These effects were blocked by the presence of combined linoleic acid and conjugated linoleic acid. Mechanistically, the expression levels of COX-1, COX-2 and NF-κB p65 in RAW264.7 cells were reduced by the presence of combined linoleic acid (100 nM) and conjugated linoleic acid (100 nM) (FIGS. 9A and B).

These results support the view that combinations of linoleic acid and conjugated linoleic acid, particularly when used at the ratios employed in these examples, express a potent-synergistic effect on inflammatory processes, including inflammatory processes involved in skin disorders such as plaque psoriasis.

Example 2. Evaluation of Combinations of Linoleic Acid and Conjugated Linoleic Acid on Transepithelial/Transendothelial Electrical Resistance Transepithelial/transendothelial electrical resistance (TEER) is a widely accepted quantitative technique to measure the integrity of tight junction dynamics in cell culture models of endothelial and epithelial monolayers. TEER values are strong indicators of the integrity of the cellular barriers before they are evaluated for transport of drugs or chemicals. This study was undertaken to evaluate the impact of LCA and CLCA, differing ratios of LCA and CLCA, and LCA/CLCA in an emollient base, on transepithelial/transendothelial electrical resistance.

The study was conducted as follows:

| | |
|---|---|
| 1 | Set up Franz Diffusion Cells ("FDCs") with a 3.3 mL receptor volume and 0.55 cm$^2$ surface area. |
| 2 | Use PBS at pH 7.4 w/2 wt % hydroxypropyl-b-cyclodextrin and 0.01 wt % NaN$_3$ as the receptor fluid. |
| 3 | Place FDCs in a dry block heater set at 32° C. The receptor fluid is continually agitated with a stir bar. |
| 4 | Allow the FDCs to equilibrate for 20 minutes. |
| 5 | Add 150 ml of PBS to the donor chamber of the FDCs. Measure TEER. |
| 6 | Remove the PBS and tap the skin dry. |
| 7 | Remove the skin from the FDCs and tapestrip three times. |
| 8 | Reassemble the FDCs with the tapestripped skin. |
| 9 | Add 150 ml of PBS to the donor chamber of the FDCs. Measure TEER. |
| 10 | Remove the PBS and tap the skin dry. |
| 11 | Dose the cells with 5 uL of formulation. |
| 12 | Wait 1 hr. |
| 13 | Add 150 ml of PBS to the donor chamber of the FDCs. Measure TEER. |
| 14 | Remove the PBS and tap the skin dry. |
| 15 | Wait 7 hrs. |
| 16 | Add 150 ml of PBS to the donor chamber of the FDCs. Measure TEER. |
| 17 | Remove the PBS and tap the skin dry. |

The results are reported in FIGS. 10 and 11.

Example 3. Evaluation of Combinations of Linoleic Acid and Conjugated Linoleic Acid on Transepidermal Water Loss Transepidermal water loss (TEWL) is a key indicator of the skin barrier function and the ability to measure this accurately is essential in a wide range of clinical and personal care applications. This study was undertaken to evaluate the impact of LCA and CLCA, differing ratios of LCA and CLCA, and LCA/CLCA in an emollient base, on transepidermal water loss.

The study was conducted as follows:

| | |
|---|---|
| 1 | Set up Franz Diffusion Cells ("FDCs") with a 3.3 mL receptor volume and 0.55 cm$^2$ surface area. |
| 2 | Use PBS at pH 7.4 w/2 wt % hydroxypropyl-b-cyclodextrin and 0.01 wt % NaN$_3$ as the receptor fluid. |

13

-continued

| | |
|---|---|
| 3 | Place FDCs in a dry block heater set at 32° C. The receptor fluid is continually agitated with a stir bar. |
| 4 | Allow the FDCs to equilibrate for 20 minutes. |
| 5 | Add Acetone on top of the skin dry out the skin's top layer |
| 6 | Check TEWL |
| 7 | Dose the cells with 5 uL of formulation. |
| 8 | Wait 2 hours then check TEWL again |
| 9 | Wait 2 more hours (4 total from dosing) then check TEWL again |

Formulations tested are described in Tables A and B:

TABLE A

| | F01 | F02 | F03 | F04 | F05 | F06 | F07 | F08 | F09 | F10 |
|---|---|---|---|---|---|---|---|---|---|---|
| LA | 100.00 | 75.00 | 67.00 | 50.00 | 33.00 | 25.00 | | | 0.50 | 0.50 |
| CLA | | 25.00 | 33.00 | 50.00 | 67.00 | 75.00 | 100.00 | | | |
| EpiCeram | | | | | | | | 100.00 | 99.40 to pH 4.5 | 96.90 to pH 4.5 |
| Lactobionic acid | | | | | | | | | | |
| PBN | | | | | | | | | 0.10 | 0.10 |
| Dimethicone | | | | | | | | | | 1.50 |
| Transcutol | | | | | | | | | | 1.00 |

TABLE B

| | F10 | F11 | F12 | F13 | F14 | F15 | F16 | F17 | F18 | F19 |
|---|---|---|---|---|---|---|---|---|---|---|
| LA | 0.50 | | | | | | | | | |
| CLA | | | | | | | | | | |
| EpiCeram | 96.90 to pH 4.5 | 98.50 | 99.90 | 99.90 to pH 4.5 | 99.00 | 98.00 | 97.00 | 96.50 | 100.00 to pH 4.0 | 100.00 to pH 4.5 |
| Lactobionic acid | | | | | | | | | | |
| PBN | 0.10 | | 0.10 | 0.10 | | | | | | |
| Dimethicone | 1.50 | 1.50 | | | | | | 1.50 | | |
| Transcutol | 1.00 | | | | 1.00 | 2.00 | 3.00 | 2.00 | | |

The results are reported in FIGS. 12, 13, and 14.

A further investigation was undertaken to evaluate the effect of pH on the trans-epidermal water loss from the formulations of this disclosure. Formulations tested are described in the Table C (wt/wt %):

TABLE C

| | F036 | F037 | F038 | F040 | F041 | F042 |
|---|---|---|---|---|---|---|
| Linoleic acid | 24.00 | 24.00 | 24.00 | 24.00 | 24.00 | 24.00 |
| Conjugated linoleic acid | 24.00 | 24.00 | 24.00 | 24.00 | 24.00 | 24.00 |
| Cetostearyl alcohol | 5.00 | 5.00 | 5.00 | 5.00 | 5.00 | 5.00 |
| Mineral oil | 10.00 | 10.00 | 10.00 | 10.00 | 10.00 | 10.00 |
| Peg 40 hydrogenated oil | 4.00 | 4.00 | 4.00 | 4.00 | 4.00 | 4.00 |
| Lactobionic acid | 0.50 | 0.50 | 0.50 | 0.50 | 0.50 | 0.50 |
| Water LC/MS | 31.70 | 31.50 | 31.30 | 31.10 | 30.70 | 30.50 |
| IN NaOH | 0.80 | 1.00 | 1.20 | 1.40 | 1.80 | 2.00 |
| pH | 4.18 | 4.45 | 4.65 | 4.71 | 5.22 | 5.35 |

The results are reported in FIG. 15.

REFERENCES CITED

1. Abdelhamid R E, Sluka K A (2015). ASICs mediate pain and inflammation in musculoskeletal diseases. Physiology 30:449-459.

2. Berenbaum F (2013) Osteoarthritis as an inflammatory disease (osteoarthritis is not osteoarthrosis!). Osteoarthritis Cartilage. 21:16-21.
3. Pomari E, Stefanon B, Colitti M (2014) Effect of plant extracts on $H_2O_2$-induced inflammatory gene expression in macrophage. J Inflamm Res. 27:103-112.
4. Kong L, Smith W, Hao D (2019) Overview of RAW264.7 for osteoclastogenesis study: Phenotype and stimuli, J Cell Mol Med 23:3077-3087.
5. Yamaguchi M, Levy R M (2020) Metaxalone suppresses production of inflammatory cytokines associated with painful conditions in mouse macrophages RAW264.7 cells in vitro: Synergistic effect with β-caryophyllene. Curr Mol Med 20:643-652.
6. Xu Y, Wang X, Liu L, Wang H, Wu H, Sun C (2022) Role of macrophages in tumor progression and therapy (Review). Int J Oncol 60:57-75.
7. Geindreau M, Bruchard M, Vegran F (2022) Role of cytokines and chemokines in angiogenesis in a tumor context. Cancers 14:2446. Doi.org/10: 3390/cancers14102446.
8. Hartley J W, Evanse L H, Green K Y, Naghashfar Z, Macias A R, Zerfas P M, Ward J M (2008) Expression of infectious murine leukemia viruses by RAW264.7 cells, a potentiated complication for studies with a widely used mouse macrophage cell line. Retrovirology 5:1.
9. Li Y, Zhang J, Yan C, Chen Q, Xiang C, Zhang Q, Wang X, Jiang K (2022) Martin prevented LPS-induced osteoclastogenesis by regulating the NF-κB pathway in vitro. J Mem Biotech 32:141-148.
10. Maldonado R F, Sa-Correia I, Valvano MA480-493 (2016) Lipopolysaccharide modification in Gram-negative bacteria during chronic infection. FEMS Microbiol Rev 40:480-493.
11. Ohanian S H, Schwab J H (1967) Persistence of group a streptococcal cell walls related in chronic inflammation of rabbit dermal connective tissue. J Exp Med 125:1137-1148
12. Whelan J, Fritsche K (2013) Linoleic acid, Advances in Nutrition 4:311-312.

13. Kiezel-Tsugunova M, Kendall A C, Nicolaou A (2018) Fatty acids and related lipid mediators in the regulation of cutaneous inflammation. Biochem Soc Trans 46:119-129.

14. Letawe C, Boone M, Pierard G E (1998) Digital image analysis of the effect of topically applied linoleic acid on acne micro components. Clinical Experimental Dermatology 23:56-58.

15. Ando H, Ryu A, Hashimoto A, Oka Ma, Ichihashi M (1998) Linoleic acid and α-linoleic acid lightens ultraviolet-induced heperpigmentation of the skin. Arch Dermatol Res 290:375-381.

16. Ochoa J J, Farquharson A J, Grant I, Moffat L E, Heys S D, Wahle K W (2004) Conjugated linoleic acids (CLAs) decrease prostate cancer cell proliferation: different molecular mechanisms for cis-9, trans-11 and trans-10, cis-12 isomers. Carcinogenesis 25:1185-1191.

17. Ma N, Chang G, Huang J, Gao Q, Cheng X, Liu J, Shen X (2019) cis-9, trans-11-conjugated linoleic acid exerts an anti-inflammatory effect in bovine mammary epithelial cells after *Escherichia coli* stimulation through NF-κB signaling pathway. J Agric Food Chem 67:193-200.

Throughout this application, various publications are referenced. The disclosures of these publications in their entireties are hereby incorporated by reference into this application in order to more fully describe the state of the art to which this disclosure pertains. It will be apparent to those skilled in the art that various modifications and variations can be made in the present disclosure without departing from the scope or spirit of the disclosure. Other embodiments of the disclosure will be apparent to those skilled in the art from consideration of the specification and practice of the disclosure disclosed herein. It is intended that the specification and examples be considered as exemplary only, with a true scope and spirit of the disclosure being indicated by the following claim.

The invention claimed is:

1. An emollient composition comprising:
(a) a 3-component combination of
(i) a LA/CLA combination, wherein the linoleic acid and the conjugated linoleic acid are present at a weight ratio of from 2:1 to 1:2,
(ii) a ceramide, and
(iii) a cholesterol, and
(b) an emollient base,
wherein the linoleic acid and the conjugated linoleic acid are the only polyunsaturated fatty acids present in the emollient composition.

2. The composition of claim 1, wherein the emollient composition comprises the ceramide, the LA/CLA combination, and the cholesterol in a physiologically balanced ratio of (3±10%): (1±10%): (1±10%).

3. The composition of claim 1, further comprising water, wherein the emollient composition comprises from 25 to 50 wt. % emollient base, and from 50 to 75 wt. % water.

4. The composition of claim 1, further comprising water, wherein the emollient composition comprises from 25 to 50 wt. % emollient base, from 50 to 75 wt. % water, and wherein the 3-component combination is present in an amount of from 1 to 10 wt. % of the emollient composition.

5. The composition of claim 1, wherein the emollient composition has a pH of from 4.2 to 4.85.

6. The composition of claim 1, wherein the emollient composition is an emulsion that further comprises water, glyceryl stearate, squalene, glycerin, PEG-100 stearate, petrolatum, dimethicone, phenoxyethanol, citric acid, palmitic acid, xanthan gum, potassium hydroxide, disodium EDTA, sorbic acid, capric acid, and one or more additional lipids.

7. The composition of claim 1, wherein the linoleic acid and conjugated linoleic acid are present at a weight ratio of about 1:1.

* * * * *